(12) United States Patent
Yuan et al.

(10) Patent No.: US 8,426,616 B2
(45) Date of Patent: Apr. 23, 2013

(54) TRIPTOLIDE LACTONE RING DERIVATIVES AS IMMUNOMODULATORS AND ANTICANCER AGENTS

(75) Inventors: Hongwei Yuan, Burlingame, CA (US); John H. Musser, San Carlos, CA (US); Dongcheng Dai, Mountain View, CA (US)

(73) Assignee: Pharmagenesis, Inc., Redwood City, CA (US)

( * ) Notice: Subject to any disclaimer, the term of this patent is extended or adjusted under 35 U.S.C. 154(b) by 152 days.

(21) Appl. No.: 12/874,434

(22) Filed: Sep. 2, 2010

(65) Prior Publication Data

US 2010/0331554 A1  Dec. 30, 2010

Related U.S. Application Data

(62) Division of application No. 10/591,358, filed as application No. PCT/US2005/006952 on Mar. 2, 2005, now Pat. No. 7,863, 464.

(60) Provisional application No. 60/549,769, filed on Mar. 2, 2004.

(51) Int. Cl.
C07D 307/77 (2006.01)

(52) U.S. Cl.
USPC .......................................................... 549/297

(58) Field of Classification Search ............ 549/297
See application file for complete search history.

(56) References Cited

U.S. PATENT DOCUMENTS

| | | | |
|---|---|---|---|
| 4,005,108 A | 1/1977 | Kupchan et al. |
| 5,192,817 A | 3/1993 | Takaishi et al. |
| 5,294,443 A | 3/1994 | Lipsky et al. |
| 5,430,054 A | 7/1995 | Qian et al. |
| 5,468,772 A | 11/1995 | Xu et al. |
| 5,580,562 A | 12/1996 | Lipsky et al. |
| 5,648,376 A | 7/1997 | Strobel et al. |
| 5,663,335 A | 9/1997 | Qi et al. |
| 5,759,550 A | 6/1998 | Wiedmann et al. |
| 5,843,452 A | 12/1998 | Wiedmann et al. |
| 5,919,816 A | 7/1999 | Hausher et al. |
| 5,962,516 A | 10/1999 | Qi et al. |
| 5,972,998 A | 10/1999 | Jung et al. |
| 6,004,999 A | 12/1999 | Jung et al. |
| 6,011,042 A | 1/2000 | Greenwald et al. |
| 6,103,875 A | 8/2000 | Martinez-Miller et al. |
| 6,150,539 A | 11/2000 | Musser et al. |
| 6,294,546 B1 | 9/2001 | Rosen et al. |
| 6,329,148 B1 | 12/2001 | Rosen et al. |
| 6,458,537 B1 | 10/2002 | Staub et al. |
| 6,537,984 B2 | 3/2003 | Rosen et al. |
| 6,548,537 B1 | 4/2003 | Dai et al. |
| 6,569,893 B2 | 5/2003 | Dai et al. |
| 6,599,499 B1 | 7/2003 | Rosen et al. |
| 6,620,843 B2 | 9/2003 | Fidler et al. |
| 6,777,441 B2 | 8/2004 | Wang et al. |
| 6,943,259 B2 | 9/2005 | Dai et al. |
| 7,019,151 B2 | 3/2006 | Dai et al. |
| 7,098,348 B2 | 8/2006 | Dai et al. |
| 7,417,069 B2 | 8/2008 | Dai et al. |
| 2002/0077350 A1 | 6/2002 | Babish et al. |
| 2002/0099051 A1 | 7/2002 | Fidler et al. |
| 2004/0018260 A1 | 1/2004 | Ren et al. |
| 2004/0152767 A1 | 8/2004 | Dai et al. |
| 2004/0198808 A1 | 10/2004 | Dai et al. |
| 2004/0235943 A1 | 11/2004 | Dai et al. |
| 2004/2883645 | 12/2005 | LaVon |
| 2007/0244080 A1 | 10/2007 | Fidler et al. |
| 2007/0249048 A1 | 10/2007 | Dai et al. |
| 2007/0282114 A1 | 12/2007 | An et al. |
| 2008/0287530 A1 | 11/2008 | Yuan et al. |

FOREIGN PATENT DOCUMENTS

| | | |
|---|---|---|
| CN | 1052859 A | 7/1991 |
| CN | 1317248 A | 10/2001 |
| EP | 0156643 B1 | 10/1985 |
| JP | 03-178977 | 8/1991 |
| WO | WO94/26265 A1 | 11/1994 |
| WO | WO97/31920 | 9/1997 |
| WO | WO97/31921 | 9/1997 |
| WO | WO98/52933 | 11/1998 |
| WO | WO98/52951 | 11/1998 |
| WO | WO00/12483 | 3/2000 |
| WO | WO00/63212 | 10/2000 |
| WO | WO02/017931 A1 | 7/2002 |
| WO | WO 02/070472 * | 9/2002 |
| WO | WO02/070472 A1 | 9/2002 |

(Continued)

OTHER PUBLICATIONS

Anderson et al., "Synthesis, Evaluation of Chemical Reactivity, and Murine Antineoplastic Activity of 2-Hydroxy-5-(3,4-dichlorophenyl)-6,7-bis(hydroxymethyl)-2,3-dihydro-1 H-pyrrolizine Bis(2-propylcarbamate) and 2-Acyloxy Derivatives as Potential Water-Soluble Prodrugs", Med. Chem., vol. 26, pp. 1333-1338 (1983).

Aumuller, et al, "Intermediate filaments in sertoli cells", Microscopy Research and Technique, vol. 20, pp. 50-72 (1992).

Becker, et al., "Thioredoxin reductase as a pathophysiological factor and drug target", Eur. J. Biochem., vol. 26, No. 20, pp. 6118-6125 (2000).

Berg, et at, "14-3-3 Proteins in the ne~ous system", Nature Reviews Neuroscience, vol. 4, pp. 752-762 (2003).

Britton, et al., "New okadaic acid analogues from the marine sponge Merriamum oxeato and their effect on mitosis", J. Nat. Prod., vol. 66, pp. 838-431 (2003).

Chang, et al., "Triptolide and chemotherapy cooperate in tumor cell apoptosis: A role for the p53 pathway", The Journal of Biological Chemistry, vol. 276, No. 3, pp. 2221-2227 (2001).

(Continued)

*Primary Examiner* — Nizal Chandrakumar
(74) *Attorney, Agent, or Firm* — McDermott Will & Emery LLP; Susan J. Myers Fitch

(57) ABSTRACT

Disclosed are compounds based on lactone ring modifications of triptolide and hydroxylated triptolide, for use in therapy, such as antiproliferative, anticancer, and immunosuppressive therapy.

13 Claims, 4 Drawing Sheets

FOREIGN PATENT DOCUMENTS

| WO | WO02/074759 A1 | 9/2002 |
|----|----|----|
| WO | WO03/101951 A2 | 12/2003 |
| WO | WO2005/000291 A1 | 1/2005 |
| WO | WO2005/020887 A1 | 3/2005 |
| WO | WO2005/062913 A2 | 7/2005 |
| WO | WO2005/084365 A2 | 9/2005 |
| WO | WO2006/012204 A2 | 2/2006 |

OTHER PUBLICATIONS

Chen, et al., "Mechanisms of tolerance induced by PG490-88 in a bone marrow transplantation model", Transplantation, vol. 73, No. 1, pp. 115-121 (2002).

Chen, et al., "Improved Preparation of Triptolide Extract", Chinese Journal of Pharmaceutcials, vol. 20, No. 5, pp. 195 and 200 (Dec. 31, 1989) *English translation of abstract and concise explanation of relevance from Foreign Office Action*.

Chen, et al., "Prevention of graft-versus-host disease by a novel immunosuppressant, PG490-88, through inhibition of alloreactive T cell expansion", Transplantation, vol. 70, No. 10, pp. 1442-1447 (2000).

Cheng, et al, "Research on extraction technology of *Tripterygium*", Chinese Journal of Phannaceuticals, vol. 21, No. 10, pp. 435-436 (1990) *No English translation*.

Cheng, et al., Yao Xue Xue Bao, ACTA Pharmaceutica Sinica, vol. 37, 339-342 (2002) *English Abstract translation*.

De Groot Franciscus, et al., "Synthesis and Biological Evaluation of 2'-Carbamate-Linked and 2'Carbonate-Linked Prod rugs of Paclitaxel: Selective Activation by the Tumor-Associated Protease Plasmin", J. Med. Chem., vol. 43, pp. 3093-3102 (2000).

De Quan, et al., "Chemical Transformation of Triptolide", Chinese Chemical Letters, vol. 2, No. 12, pp. 937-940 (1991).

Dittert, et al., "Acetaminophen Prodrugs I Synthesis, Physicochemical Properties, and Analgesic Activity", Journal of Phannaceutical Sciences, vol. 5, No. 5, pp. 774-780 (1968).

Dittert, et al., "Acetaminophen Prodrugs II Effect of Structure and Enzyme Source on Enzymatic and Nonenzymatic Hydrolysis of Carbonate Esters," J. of Phann. Sciences, vol. 5, No. 5, pp. 780-783 (1968).

Englebienne et al., Drug Design Reviews—Online, "The Place of Biosteric Sila Substitution in Drug Design", 2 pages (2005).

Fidler, et al., "PG490-88, a derivative of triptolide, causes tumor regression and sensitizes tumors to chemotherapy", Molecular Cancer Therapeutics, vol. 2, No. 9, pp. 855-862 (2003).

Fidler, et al., "Immunosuppressive activity of the Chinese medicinal plant *Tripterygium wilfordii*. III. Suppression of graft-versus-host disease in murine allogeneic bone marrow transplantation by the PG27 extract", Transplantation, vol. 74, No. 4, pp. 445-457 (2002).

Fruman, et al., "Phosphoinositide Kinases", Ann. Rev. Biochem., vol. 67, pp. 481-507 (1998).

Fu, et al., "14-3-3 Proteins: Structure, Function, and regulation", Ann. Rev. Pharmacol. Toxicol., vol. 40, pp. 617-647 (2000).

Gabbiani, "The myofibroblast in wound healing and fibrocontractive diseases", Journal of Pathology, vol. 200, pp. 500-503 (2003).

Garcia, et al., "Serine/threonine protein phosphatases PP1 and PP2A are key players in apoptosis", Biochimie, vol. 85, pp. 721-726 (2003).

Gilles, et al., "Transactivation of vimentin by beta-catenin in human breast cancer cells", Cancer Research, vol. 63, No. 10, pp. 2658-2664 (2003).

Gleichmann, et al., "Graft-versus-host reactions: clues to the etiopathology of a spectrum of immunological diseases", Immuno/ogy Today, vol. 5, No. 11, pp. 324-332 (1984).

Goto, et al., "Augmented cytoplasmic Smad4 induces acceleration of TGF-beta1 signaling in renal tubulointerstitial cells of hereditary nephrotic ICGN mice with chronic renal fibrosis; possible role for myofibroblastic differentiation", Cell Tissue Res., vol. 315, pp. 209-221 (2004).

Gross and Hunninghake, "Idiopathic pulmonary fibrosis", N. Engl. J. Med., vol. 345, No. 7, pp. 517-525 (2001).

Gu, et al., "Effect of Chinese herb *Tripterygium wilfordii* Hook F monomer triptolide on apoptosis of PC12 cells induced by A$\beta$1-42" ACTA Physiologica Sinica, vol. 56, No. 1, pp. 73-78 (2004) *English Abstract translation*.

Hansen et al., "Carbamate Ester Prodrus of Dopaminergic Compounds: Synthesis, Stability, and Bioconversion", Journal of Pharmaceutical Sciences, vol. 80, No. 8, pp. 793-798 (1991).

Hansen et al., "Ketobemidone prodrugs for buccal delivery", Acta Pharm. Nord., vol. 3, No. 2, pp. 77-82 (1991).

He, et al., "Neuroprotective eggects of *Tripterygium wilfordii* Hook F Monomer $T_{10}$ on glutamate induced PC12 cell line damage and its mechanism", Beijing Da Xue Xue Bao, Journal of Peking University, Health Sciences, vol. 35, No. 3, pp. 252-255 (2003) *English Abstract Translation*.

Houtman, et al., "Early phosphorylation kinetics of proteins involved in proximal TCR-mediated signaling pathways", Journal of Immunology, vol. 175, No. 4, pp. 2449-2458 (2005).

Huang, et al., "Hydrolysis of Carbonates, Thiocarbonates, Carbamates, and Carboxylic Esters of $\alpha$-Naphthol, $\beta$-Naphthol, and p-Nitrophenol by Human, Rat, and Mouse Liver Carboxylesterases", Pharmaceutical Research, vol. 10, No. 5, pp. 639-648 (1993).

Jiang, et al., "Functional p53 is required for triptolide-induced apoptosis and AP-1 and nuclear factor-kappaB activation in gastric cancer cells",Oncogene, vol. 20, No. 55, pp. 8009-8018 (2001).

Jerums, et al., "Evolving concepts in advanced glycation, diabetic nephropathy, and diabetic vascular disease", Archives of Biochemistry and Bipphysics, vol. 419, No. 1, pp. 55-62 (2003).

Jiarun, et al., "Screening of active anti-inflammatory, immunosuppressive and antifertility components of *Tripterygium wilfordii*", ACTA Academiae Medicinae Sinicae, vol. 13, No. 6, pp. 391-397 *English Abstract only* (1991).

Jones, et al., "A role for the actin-bundling protein L-plastin in the regulation of leukocyte integrin function", Proc. Natl. Acad. Sci. USA, vol. 95, No. 16, pp. 9331-9336 (1998).

Kahns, et al., "Prodrugs of Peptides. 18. Synthesis and Evaluation of Various Esters of Desmopressin (dDAVP)", Pharmaceutical Research, vol. 10, No. 1, pp. 68-74 (1993).

Kershenobich, et al., "Concise Review: Liver fibrosis and inflammation. A review", Annals of. Hepatology, vol. 4, No. 4, pp. 159-163 (2003).

Keyser, et al., "The role of T cells in Rheumatoid Arthritis", Clinical Rheumatology, vol. 14, Suppl. 2, pp. 5-9 (1995).

Khanna and Mehta, "Targeted in-vitro and in-vivo gene transfer into T lymphocytes: potential of direct inhibition of allo-immune activation", BMC Immunology, vol. 7, No. 26, pp. 1-10 (2006).

Korngold and Sprent, "Lethal graft-versus-host disease after bone marrow transplantation across minor histocompatibility barriers in mice: Prevention by removing mature T cells from marrow", J. Exp. Med., vol. 148, pp. 1687-1698 (1978).

Krishna, et al., "PG490-88, a derivative of triptolide, blocks bleomycin-induced lung fibrosis", Am. J. Pathology, vol. 158. No. 3, pp. 997-1004 (2001).

Kupchan, et al., "Triptolide and tripdiolide, novel antileukemic diterpenoid triepoxides from *Tripterygium wilfordii*", American Chemical Society, vol. 94, No. 20, pp. 7194-7195 (1972).

Kurz, et al., "Modulation of human DNA topoisomerase llalpha function by interaction with 14-3-3 epsilon", The Journal of Biological Chemistry, vol. 275, No. 18, pp. 13948-13954 (2000).

Kutney, et al., "Studies with plant cell cultures of the Chinese herbal plant, *Tripterygium wilfordii*, Synthesis and biotransformation of diterpene analogues", Heterocycles, vol. 44, No. 1, pp. 2-11 (1997).

Larribere, et al., "PI3K mediates protection against TRAIL-induced apoptosis in primary human melanocytes", Cell Death and Differentiation, vol. 11, No. 10, pp. 1084-1091 (2004).

Leonard, et al., "PG490-88, a derivative of triptolide, attenuates obliterative airway disease in a mouse heterotopic tracheal allograft model", Journal of Heart and Lung Transplantation, vol. 21, No. 12, pp. 1314-1318 (2002).

Leuenroth and Crews, "Studies on calcium dependence reveal multiple modes of action for triptolide", Chemistry and Biology, vol. 14, No. 12, pp. 1259-1268 (2005).

Li and Fidler, "PG490-88 erxerts 1-16 potent anticancer activity alone and in combination therapy in a nude mouse xenograft model", Proceedings of theAmerican Association for Cancer Research Annual Meeting Mar. 2001, vol. 42, p. 73, Abstract #391 (2001).

Li, et al., "Neurotrophic and neuroprotective effects of tripchlorolide, an extract of Chinese herb *Tripterygium wilfordii* Hook F, on dopaminergic neurons", Experimental Neurology, vol. 179, No. 1, pp. 28-37 (2003).

Li, et al., "Triptolide, a Chinese herbal extract, protects dopaminergic neurons from inflammation-mediated damage through inhibition of microglial activation", Journal of Neuroimmunology, vol. 148, No. 1-2, pp. 24-31 (2004).

Lin, et al., "Upregulation of L-plastin gene by testosterone in breast and prostate cancer cells: identification of three cooperative androgen receptor-binding sequences", DNA Cell Biology, vol. 19, No. 1, pp. 1-7 (2000).

List, et al., "Vascular endothelial growth factor receptor-1 and receptor-2 initiate a phosphatidylinositide 3-kinase-dependent clonogenic response in acute myeloid leukemia cells.", Experimental Hematology, vol. 32, No. 6, pp. 526-535 (2004).

Lovell, et al., "Decreased thioredoxin and increased thioredoxin reductase levels in Alzheimer's disease brain", Free Radical Biology & Medicine, vol. 28, No. 3, pp. 418-427 (2000).

Lundstrom, et al., "A Pro to His mutation in active site of thioredoxin increases its disulfide-isomerase activity 10-fold. New refolding systems for reduced or randomly oxidized ribonuclease", The Journal of Biological Chemistry, vol. 267, No. 13, 9047-9052 (1992).

Lundy, et al., "Cells of the synovium in rheumatoid arthritis". Arthritis Research & Therapy, vol. 9, No. 1, pp. 1-11 (2007).

Mason, et al., "Pharmacological therapy for idiopathic pulmonary fibrosis". Am. J. Respir. Crit. Care Med., vol. 160, pp. 1771-1777 (1999).

Masters and Fu, "14-3-3 Proteins mediate an essential anti-apoptotic signal", The Journal of Biological Chemistry, vol. 276, No. 48, pp. 45193-45200 (2001).

Matlin, et al., "Male antifertility compounds from *Tripterygium wilfordii* Hook F", Contraception, vol. 47, pp. 387-400 (1993).

Mesa, et al., "In vitro anti proliferative activity of the farnesyltransferase inhibitor R 115777 in hematopoietic progenitors from patients with myelofibrosis with myeloid metaplasia", Leukemia, vol. 17, No. 5, pp. 849-855 (2003).

Murase, et al., "Hamster-to-rat heart and liver xenotransplantation with FK506 plus antiproliferative drugs", Transplantation, vol. 55, No. 4, pp. 701-708 (1993).

Nassar, et al., "Effects of Structural Variations on the Rates of Enzymatic and Nonenzymatic Hydrolysis of Carbonate and Carbamate Esters", Journal of Pharmaceutical Sciences, vol. 81, No. 3, 295-298 (1992).

Ning, et al., "Biotransformation of triptolide by *Cunninghamella blakesleana*", Tetrahedron, vol. 56, No. 23, pp. 4209-4213 (2003).

Ono and Lindsey, "Improved technique of heart transplantation in rats", Journal of Thoracic and Cardiovascular Surgery, vol. 57, No. 2, pp. 225-229 (1969).

Ory, et al., "Protein phosphatase 2A positively regulates Ras signaling by dephosphorylating KSR1 and Raf-1 on critical 14-3-3 binding sites", Current Biology, vol. 13, No. 16, pp. 1356-1364 (2003).

Otsuka, et al., "Differential expression of the L-plastin gene in human colorectal cancer progression and metastasis", Biochemical and Biophysical Research Communications, vol. 289, No. 4, pp. 876-881 (2001).

Pei, et al., "Okadaic-acid-induced inhibition of protein phosphatase 2A produces activation of mitogen-activated protein kinases ERK1/2. MEK1/2. and p70 S6 similar to that in Alzheimer's disease", American Journal of Pathology, vol. 163, No. 3, pp. 845-858 (2003).

Powis and Montfort, "Properties and biological activities of thioredoxins", Ann.Rev. Pharmacol. Toxicol., vol. 41, pp. 261-295 (2000).

Qiu and Kao, "Immunosuppressive and anti-inflammatory mechanisms of triptolide: The principal active diterpenoid from the Chinese medicinal herb *Tripterygium wilfordii* Hook F", Drugs R&D, vol. 4, No. 1, pp. 1-18 (2003).

Qiu, et al., "Immunosuppressant PG490 (triptolide) inhibits T-cell interleukin-2 expression at the level of purine-box/nuclear factor of activated T-cells and NF kappa8 transcriptional activation", The Journal of Biological Chemistry, vol. 274, No. 19, pp. 13443-13450 (1999).

Redpath, et al., "Regulation of translation elongation factor-2 by insulin via a rapamycine-sensitive Signalling pathway", The EMBO Journal, vol. 15, No. 9, pp. 2291-2297 (1996).

Reichert, et al., "Interleukin-2 expression in human carcinoma cell lines and its role in cell cycle progression", Oncogene, vol. 19, No. 4, 514-525 (2000).

Sato, et al., "Modulation of Akt kinase activity by binding to Hsp90", Proc. Natl. Acad. Sci. USA, vol. 97, No. 20, pp. 10832-10837 (2000).

Savolainen, et al., "Synthesis and in vitro/in vivo evaluation of novel oral N-alkyl- and N,N-dialkyl-carbamate esters of entacapone", Life Sciences, vol. 67, pp. 205-216 (2000).

Schlesinger, et al., "Constrictive (obliterative) bronchiolitis: diagnosis, etiology and a critical review of the literature", Annals of Diagnostics Pathology, vol. 2, No. 5, pp. 321-334 (1998).

Schlesinger, et al., "Constrictive (obliterative) bronchiolitis", Current Opinion in Pulmonary Medicine, vol. 4, pp. 288-293 (1998).

Schwaller, et al., "Reduction-reoxidation cycles contribute to catalysis of disulfide isomerization by protein-disulfide isomerase", The Journal of Biological Chemistry, vol. 278, No. 9, pp. 7154-7159 (2003).

Selman, et al., "Idiopathic pulmonary fibrosis: prevailing and evolving hypotheses about its pathogenesis and implications for therapy", Ann. Intern. Med., vol. 134, pp. 136-151 (2001).

Shamon, et al., "Evaluation of the mutagenic, cytotoxic, and antitumor potential of triptolide, a highly oxygenated diterpene isolated from *Tripterygium wilfordii*", Cancer Letters, vol. 112, pp. 113-117 (1997).

Shanmuganathan, et al., "Enhanced brain delivery of an anti-HIV nucleoside 2'-Fara-ddl by xanthine oxidase mediated biotransformation", J. Med. Chem., vol. 37, pp. 821-827 (1994).

Shevchenko, et al., "Mass spectrometric sequencing of proteins silver-stained polyacrylamide gels", Anal. Chem., vol. 68, No. 5, pp. 850-858 (1996).

Shevchenko, et al., "Linking genome and proteome by mass spectrometry: largescale identification of yeast proteins from two dimensional gels", Proc. Natl. Acad. Sci. USA, vol. 93, pp. 14440-14445 (1996).

Show, et al., "Reduced intratesticular testosterone concentration alters the polymerization state of the Sertoli cell intermediate filament cytoskeleton by degradation of vimentin", Endocrinology, vol. 144, No. 12, pp. 5530-5536 (2003).

Solit, et al., "Hsp90 as a therapeutic target in prostate cancer", Seminars in Oncology, vol. 30, No. 5, pp. 709-716 (2003).

Sontag, et al., "Protein phosphatase 2A is a critical regulator of protein kinase C zeta signaling targeted by SV40 small t to promote cell growth and NF-kappaB activation", The EMBO Journal, vol. 16, No. 18, pp. 5662-5671 (1997).

Stella, et al., "Prodrugs, Do they have advantages in Clinical Practice?", Drugs, vol. 29, pp. 455-473 (1985).

Textbook of Chinese Medicine Chemistry for Chinese Colleges of Traditional Chinese Medicine in the New Century (for Chinese Medicine Specialty), Kuang Hai-Xue p. 23, Chinese Press of Traditional Chinese Medicine (Jun. 30, 2003) *English translation of abstract and concise explanation of relevance from Foreign Office Action.*

Tolstonog, et al., "Role of the intermediate filament protein vimentin in delaying senescence and in the spontaneous immortalization of mouse embryo fibroblasts", DNA and Cell Biology, vol. 20, No. 9, 509-529 (2001).

Tunek, et al., "Hydrolysis of $^3$H-Bambuterol, A Carbamate Prodrug of Terbutaline, in Blood from Humans and Laboratory Animals In Vitro", Biochemical Pharmacology, vol. 3, No. 20, pp. 3867-3876 (1988).

Van Tamelen, et al., "Biogenetic-type total synthesis of (t, −)-triptonide and (.+ −.)-triptolide", STN International Database, CAPLUS database Document No. 96:143107 2 pages (1982).

Vierling, et al., "Highly fluorinated amphiphiles as drug and gene carrier and delivery systems", Journal of Fluorine Chemistry, vol. 107, pp. 337-354 (2001).

Wahlgren, et al, "Itch and inflammation induced by intradermally injected interleukin-2 in atopic dermatitis patients and healthy subjects", Arch Dermatol Res., vol. 287, No. 6, pp. 572-580 (1995).

Waller and George, "Prodrugs", Br. J. Clin. Pharmac., vol. 28, pp. 497-507 (1989).

Wang, et al., "Altered distribution of Sertoli cell vimentin and increased apoptosis in cryptorchid rats", Journal of Pediatric Surgery, vol. 37, No. 4, pp. 648-652 (2002).

Wang, et al., "Immunosuppressive activity of the Chinese medicinal plant *Tripterygium wilfordii*. I. Prolongation of rat cardiac and renal allograft survival by the PG27 extract and immunosuppressive synergy in combination therapy with cyclosporine", Transplantation, 70, No. 3, pp. 447-455 (2000).

Wang and Morris, "Effect of splenectomy and mono- or combination therapy with rapamycin, the morpholinoethyl ester of mycophenolic acid and deoxyspergualin on cardiac xenograft survival", Transplantation Proceedings, vol. 23, No. 1, pp. 699-702 (1991).

Wang, et al., "Mechanism of triptolide-induced apoptosis: Effect on caspase activation and Bid cleavage and essentiality of the hydroxyl group of triptolide", J. Mol. Med., vol. 84, pp. 405-415 (2006).

Weibel, et al., "Macromolecular prodrugs IXX. Kinetics of hydrolysis of benzyl dextran carbonate ester conjugates in aqueous buffer solutions and human plasma", Acta Pharm. Nord., vol. 3, No. 3, pp. 159-162 (1991).

Weng, et al., "Advances in studies on apoptosis induced by *Tripterygium wilfordii*", Chinese Traditional and Herbal Drugs, vol. 33, No. 11, pp. 1053-1054 (2002) *No English Abstract Translation*.

Whitesell, et al., "The stress response: implications for the clinical development of hsp90 inhibitors", Current Cancer Drug Targets, vol. 3, No. 5, pp. 349-358 (2003).

Yamagishi, et al., "Advanced glycation end products inhibit de novo protein synthesis and induce TGF-beta overexpression in proximal tubular cells", Kidney International, vol. 63, No. 2, pp. 464-473 (2003).

Yamamoto, et al., "Pharmaceutical Studies on water-Soluble corticosteroid derivatives I. Stability of Hydrocortisone 21 Hemiesters in Solution", Journal of the Pharmaceutical Society of Japan, vol. 46, No. 8, pp. 855-862 (1971).

Yang, et al., "Triptolide Induces apoptotic death of T lymphocyte", Immunopharmacology, vol. 40, pp. 139-149 (1998).

Yang, et al., "Disruption of the EF-2 kinase/Hsp90 protein complex: a possible mechanism to inhibit glioblastoma by geldanamycin", Cancer Research, vol. 61, No. 10, pp. 4010-4016 (2001).

Yang, et al., "Triptolide Inhibits the Growth and Metastasis of Solid Tumors", Molecular Cancer Therapeutics, vol. 2:65-72 (2003).

Yang, et al., Tetrahedron Letters, vol. 36, No. 39, pp. 6865-6868 (1997).

Yano, et al., "Inhibition of histamine secretion by wortmannin through the blockade of phosphatidylinositol 3-kinase in RBL-2H3 cells", The Journal of Biological Chemistry, vol. 268, No. 34, 25846-25856 (1993).

Yu, et al., Chinese Chemical Letters, vol. 4, No. 12, pp. 937-940 (1991).

Yuan, et al., "Characterization of cells from pannus-like tissue over articular cartilage of advanced osteoarthritis", OsteoArthritis and Cartilage, vol. 12, No. 1, pp. 38-45 (2004).

Zhang, et al., "Studies on Diterpenoids from leaves of *Tripterygium wilfordii*", ACTA Pharmaceutica Sinica, vol. 28, No. 2, pp. 110-115 (1993) *English Abstract translation*.

Zheng, et al., "Screening of active antiinflammatory, immunosuppressive and antifertility components of *Tripterygium wilfordii*", Chemical Abstracts, vol. 117, No. 9, Abstract No. 83085a (1992).

Zhou, et al., "Triptolide inhibits TNF-alpha, IL-1 beta and NO production in primary microglial cultures", Neuroreport, vol. 14, No. 7, pp. 1091-1095 (2003).

Zhou, et al., Ai Zheng, vol. 21, pp. 1108-1118 (2002).

Ma, et al., "16-Hydroxytriptolide: An active compound from *Tripterygium wilfordii*", J. Clin. Pharm. Sci., vol. 1, pp. 12-18 (1992).

Panchagnula and Thomas, "Biopharmaceutics and pharmacokinetics in drug research", Intl. J. Pharmaceutics, vol. 201, No. 2, pp. 131-150 (2000).

Pu, et al., "Effects of triptolide on T lymphocyte functions in mice", Acta Pharmacologica Sinica, vol. 11, No. 1, pp. 76-79 (1990).

\* cited by examiner

TRIPTOLIDE LACTONE RING DERIVATIVES AS IMMUNOMODULATORS AND ANTICANCER AGENTS

RELATED APPLICATIONS

This application is a divisional application of U.S. patent application Ser. No. 10/591,358, filed 12 Aug. 2008 under 35 U.S.C. 371 as a U.S. National Stage Entry of PCT/US2005/006952, filed 2 Mar. 2005, which claims the benefit of priority to U.S. Provisional Application Ser. No. 60/549,769, filed 2 Mar. 2004. Each of these priority applications is herein incorporated by reference in its entirety.

FIELD OF THE INVENTION

The present invention relates to compounds useful as immunosuppressive, anti-inflammatory and anticancer agents.

REFERENCES

Gleichmann, E. et al., *Immunol. Today* 5:324 (1984).
He, Q. et al., *Beijing Da Xue Xue Bao* 35:252-5 (June 2003).
Korngold, R. and Sprent, J., *J. Exp. Med.* 148:1687 (1978).
Krishna, G. et al., *Am. J. of Pathology* 158(3):997-1004 (March 2001).
Kupchan, S. M. et al., *J. Am. Chem. Soc.* 94:7194 (1972).
Kupchan, S. M. et al., U.S. Pat. No. 4,005,108 (1977).
Lipsky et al., U.S. Pat. No. 5,294,443 (1994).
Ma et al., *J. Chin. Pharm. Sci.* 1:12 (1992).
Murase, N. et al., *Transplantation* 55:701 (1993).
Ono and Lindsey, *J. Thor. Cardiovasc. Surg.* 57(2):225-29 (1969).
Panchagnula, R. and Thomas, N. S., *Intl J of Pharmaceutics* 201(2):131-150 (2000).
Pu, L. et al., *Zhongguo Yaoll Xuebao* 11:76 (1990).
Wang, J. and Morris, R. E., *Transplantation Proc.* 23:699 (1991).
Wang, X. et al., PCT Pubn. No. WO 2002/17931 (2002).
Zhou, Y. X. et al., *Ai Zheng* 21(10):1108-8 (October 2002).

BACKGROUND OF THE INVENTION

Immunosuppressive agents are widely used in the treatment of autoimmune disease and in treating or preventing transplantation rejection, including the treatment of graft-versus-host disease (GVHD). Common immunosuppressive agents include azathioprine, corticosteroids, cyclophosphamide, methotrexate, 6-mercaptopurine, vincristine, and cyclosporin A. In general, none of these drugs are completely effective, and most are limited by severe toxicity. For example, cyclosporin A, a widely used agent, is significantly toxic to the kidney. In addition, doses needed for effective treatment may increase the patient's susceptibility to infection by a variety of opportunistic invaders.

The compound triptolide, obtained from the Chinese medicinal plant *Tripterygium wilfordii* (TW), and certain derivatives and prodrugs thereof, have been identified as having immunosuppressive activity, e.g. in the treatment of autoimmune disease, and in treating or preventing transplantation rejection, including the treatment of graft-versus-host disease (GVHD). See, for example, co-owned U.S. Pat. Nos. 5,962,516 (Immunosuppressive compounds and methods), 5,843,452 (Immunotherapy composition and method), 5,759,550 (Method for suppressing xenograft rejection), 5,663,335 (Immunosuppressive compounds and methods), 5,648,376 (Immunosuppressant diterpene compound), and 6,150,539 (Triptolide prodrugs having high aqueous solubility), which are incorporated by reference. Triptolide and certain derivatives and prodrugs thereof have also been reported to show anticancer activity; see, for example, Kupchan et al., 1972, 1977, as well as co-owned U.S. Pat. No. 6,620,843 (September 2003), which is hereby incorporated by reference.

Although derivatives and prodrugs of triptolide have provided benefits relative to native triptolide in areas such as pharmacokinetics or biodistribution, e.g. by virtue of differences in lipid or aqueous solubility, or via their activity as prodrugs, the biological activity per se of triptolide derivatives is often significantly less than that of native triptolide.

SUMMARY OF THE INVENTION

In one aspect, the invention provides compounds which are useful for immunosuppressive, anti-inflammatory and anticancer therapy. The compounds are derivatives of triptolide represented by formula I:

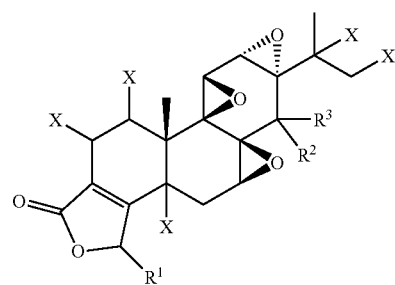

where
$R^1$ is alkyl, alkenyl, alkynyl, arylalkyl, aryl, arylacyl, or $C(OH)R^4R^5$,
wherein $R^4$ and $R^5$ are independently hydrogen, alkyl, cycloalkyl, alkenyl, or cycloalkenyl, any of which, excepting hydrogen, may be substituted with alkoxy, hydroxy, acyloxy, or aryl;
$CR^2R^3$ is CHOH or C=O, and
at most one of the groups X is hydroxyl, and the remaining groups X are hydrogen.

In preferred embodiments of structure I, $CR^2R^3$ is CHOH, preferably having the β-hydroxy configuration. In further embodiments, each group X is hydrogen.

Preferably, each said alkyl, alkenyl, alkynyl, alkoxy, and acyloxy moiety present in a compound of structure I includes at most four carbon atoms, each said cycloalkyl and cycloalkenyl moiety includes at most six carbon atoms, and each said aryl moiety is monocyclic and non-heterocyclic (i.e.; consists of hydrogen and carbon atoms).

In selected embodiments of structure I, $R^1$ is alkyl, alkenyl or $C(OH)R^4R^5$, where, preferably, each of $R^4$ and $R^5$ is independently hydrogen, alkyl or alkenyl. In further embodiments, $R^1$ is alkyl, preferably $C_1$-$C_3$ alkyl, or hydroxyalkyl. In one embodiment, $R^1$ is methyl. In another embodiment, $R^1$ is arylacyl, preferably benzoyl ($C(O)C_6H_5$).

In a related aspect, the invention provides compounds of structure II:

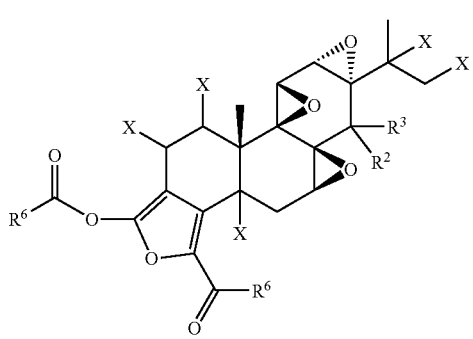

where
each $R^6$ is independently selected from alkyl, alkenyl, alkynyl, or aryl;
$CR^2R^3$ is CHOH or C=O;
at most one of the groups X is hydroxyl, and the remaining groups X are hydrogen.

In preferred embodiments of structure II, $CR^2R^3$ is CHOH, preferably having the β-hydroxy configuration. In further embodiments, each group X is hydrogen.

Preferably, each said alkyl, alkenyl, and alkynyl moiety present in a compound of structure II includes at most four carbon atoms, and each said aryl moiety is monocyclic and non-heterocyclic; e.g. substituted or unsubstituted phenyl.

In selected embodiments of structure II, each $R^6$ is aryl; preferably, each $R^6$ is unsubstituted phenyl.

In another aspect, the invention provides a method of effecting immunosuppression in a subject, by administering to a subject in need of such treatment an effective amount of a compound having the structure I or II as described above. In a further aspect, the invention provides a method of inducing apoptosis in a cell, which is useful in antiproliferative therapy, especially anticancer therapy. In accordance with this method, the cell is contacted with an effective amount of a compound having the structure I or II as described above. Alternatively, the invention encompasses the use of a compound of structure I or II for effecting immunosuppression or for inducing apoptosis in a cell, or for preparation of a medicament for effecting immunosuppression or for inducing apoptosis in a cell. The compound is typically provided in a pharmaceutically acceptable carrier. Specific embodiments of the methods and uses may employ any of the specific embodiments of formulas I and II described above.

These and other objects and features of the invention will become more fully apparent when the following detailed description of the invention is read in conjunction with the accompanying drawings.

DETAILED DESCRIPTION OF THE INVENTION

I. Definitions

Figure 1:
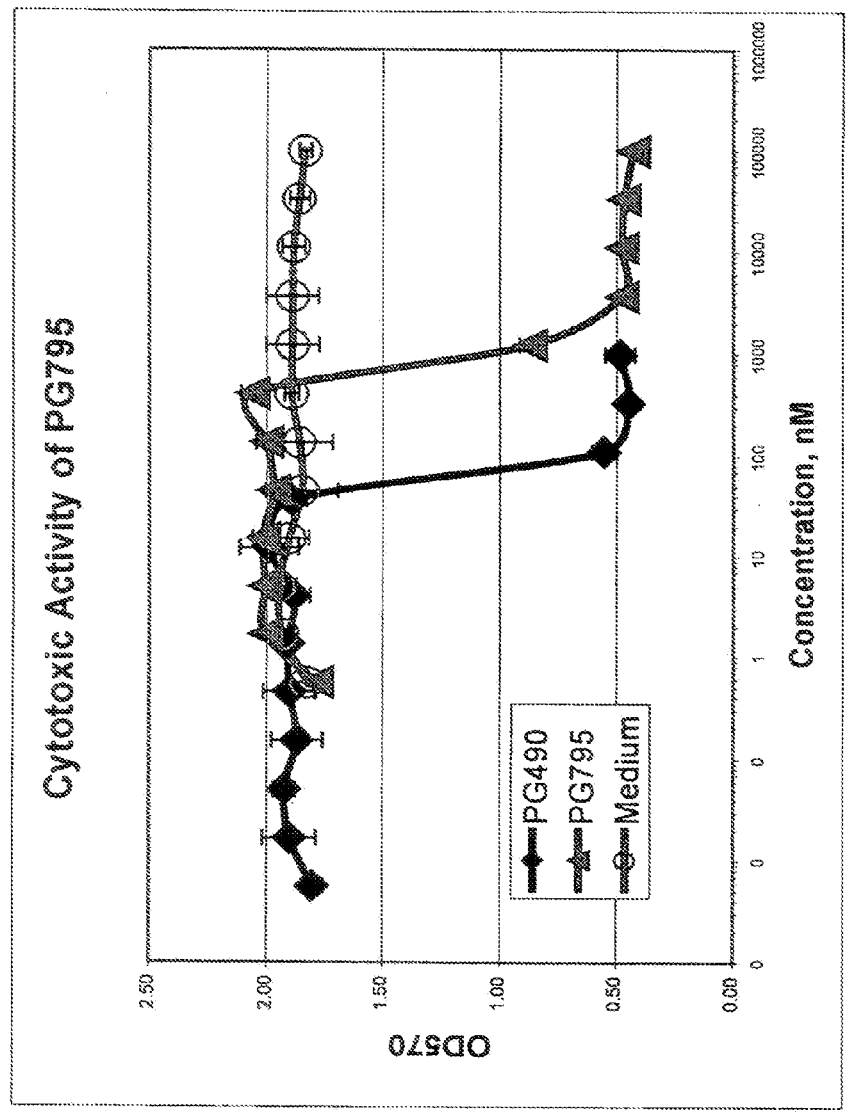
FIG. 1 shows the cytotoxic effect in Jurkat cells of a compound of the invention, 19-methyl triptolide (designated PG795), in comparison with triptolide (designated PG490) (Example 3)

"Alkyl" refers to a saturated acyclic monovalent radical containing carbon and hydrogen, which may be linear or branched. Examples of alkyl groups are methyl, ethyl, n-butyl, t-butyl, n-heptyl, and isopropyl. "Cycloalkyl" refers to a fully saturated cyclic monovalent radical containing carbon and hydrogen, which may be further substituted with alkyl. Examples of cycloalkyl groups are cyclopropyl, methyl cyclopropyl, cyclobutyl, cyclopentyl, ethylcyclopentyl, and cyclohexyl. "Lower alkyl" refers to such a group having one to six carbon atoms, preferably one to four carbon atoms.

"Alkenyl" refers to an acyclic monovalent radical containing carbon and hydrogen, which may be linear or branched, and which contains at least one carbon-carbon double bond (C=C). "Alkynyl" refers to an acyclic monovalent radical containing carbon and hydrogen, which may be linear or branched, and which contains at least one carbon-carbon triple bond (C≡C). "Lower alkenyl" or "lower alkynyl" such a group having two to six carbon atoms, preferably two to four carbon atoms.

"Acyl" refers to a radical having the form —(C=O)R, where R is alkyl (alkylacyl) or aryl (arylacyl). "Acyloxy" refers to a group having the form —O(C=O)R.

"Aryl" refers to a monovalent aromatic radical having a single ring (e.g., benzene) or two condensed rings (e.g., naphthyl). As used herein, aryl is preferably monocyclic and carbocyclic (non-heterocyclic), e.g. a benzene (phenyl) ring or substituted benzene ring. By "substituted" is meant that one or more ring hydrogens is replaced with a group such as a halogen (e.g. fluorine, chlorine, or bromine), lower alkyl, nitro, amino, lower alkylamino, hydroxy, lower alkoxy, or halo-(lower alkyl).

"Arylalkyl" refers to an alkyl, preferably lower ($C_1$-$C_4$, more preferably $C_1$-$C_2$) alkyl, substituent which is further substituted with an aryl group; examples are benzyl and phenethyl.

A "heterocycle" refers to a non-aromatic ring, preferably a 5- to 7-membered ring, whose ring atoms are selected from the group consisting of carbon, nitrogen, oxygen and sulfur. Preferably, the ring atoms include 3 to 6 carbon atoms. Such heterocycles include, for example, pyrrolidine, piperidine, piperazine, and morpholine.

For the purposes of the current disclosure, the following numbering scheme is used for triptolide and triptolide derivatives:

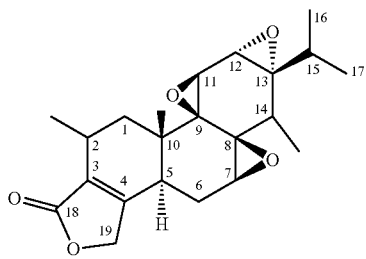 [SMILES: CC1C[C@@]2(C)[C@@H](C[C@@H]3O[C@@]34C(C)[C@@]3(C(C)C)O[C@H]3[C@@H]3O[C@]324)C2=C1C(=O)OC2]

II. Triptolide Derivatives

The compounds of the invention are derivatives of triptolide or hydroxylated triptolides, resulting from alkylation or acylation of the furanoid (lactone) ring, as described below.

More specifically, the invention provides compounds represented by structure I:

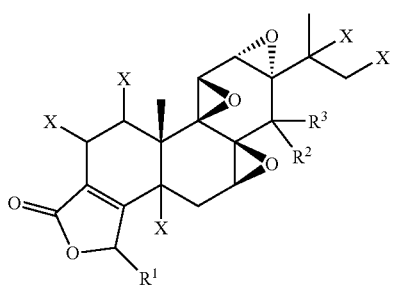

where $R^1$ is alkyl, alkenyl, alkynyl, arylalkyl, aryl, arylacyl, or $C(OH)R^4R^5$, wherein $R^4$ and $R^5$ are independently hydrogen, alkyl, cycloalkyl, alkenyl, or cycloalkenyl, any of which, excepting hydrogen, may be substituted with alkoxy, hydroxy, acyloxy, or aryl;

$CR^2R^3$ is CHOH or C=O, and at most one of the groups X is hydroxyl, and the remaining groups X are hydrogen.

In preferred embodiments of structure I, $CR^2R^3$ is CHOH, preferably having the β-hydroxy configuration.

Preferably, each X is hydrogen; however, in selected embodiments, exactly one of the indicated groups X is hydroxyl. Preferred locations for hydroxyl substitution include carbons 2 and 16, as shown in the numbering scheme above.

Preferably, each said alkyl, alkenyl, alkynyl, alkoxy, and acyloxy moiety present in a compound of structure I includes at most four carbon atoms, each said cycloalkyl and cycloalkenyl moiety includes at most six carbon atoms, and each said aryl moiety is monocyclic and non-heterocyclic.

In selected embodiments of structure I, $R^1$ is alkyl, alkenyl, alkynyl, arylalkyl, aryl, or $C(OH)R^4R^5$, preferably alkyl, alkenyl or $C(OH)R^4R^5$, where, preferably, each of $R^4$ and $R^5$ is independently hydrogen, alkyl or alkenyl. In further embodiments, $R^1$ is alkyl, preferably $C_1$-$C_3$ alkyl, or hydroxyalkyl. In one embodiment, which includes the compound designated herein as PG795, $R^1$ is methyl. In other embodiments, which include the compound 19-benzoyl triptolide, $R^1$ is arylacyl, preferably benzoyl.

In a related aspect, the invention provides compounds of structure II:

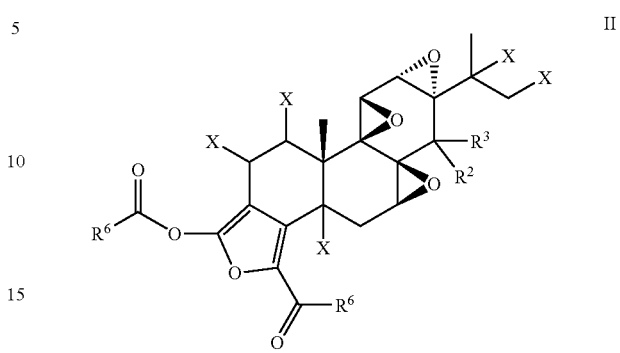

where each $R^6$ is independently selected from alkyl, alkenyl, alkynyl, or aryl;

$CR^2R^3$ is CHOH or C=O;

at most one of the groups X is hydroxyl, and the remaining groups X are hydrogen.

In preferred embodiments of structure II, $CR^2R^3$ is CHOH, preferably having the β-hydroxy configuration. Preferably, each X is hydrogen; however, in selected embodiments, exactly one of the indicated groups X is hydroxyl. Preferred locations for hydroxyl substitution include carbons 2 and 16, as shown in the numbering scheme above.

Preferably, each said alkyl, alkenyl, and alkynyl moiety present in a compound of structure II includes at most four carbon atoms, and each said aryl moiety is monocyclic and non-heterocyclic; e.g. substituted or unsubstituted phenyl.

In selected embodiments of structure II, each $R^6$ is aryl; preferably, each $R^6$ is phenyl. This includes the compound designated herein as PG796, where each $R^6$ is unsubstituted phenyl.

A. Preparation

The compounds of the invention may be prepared from triptolide or its hydroxylated derivatives. The latter include tripdiolide (2-hydroxy triptolide) and 16-hydroxy triptolide, which, along with triptolide, can be obtained from the root xylem of the Chinese medicinal plant *Tripterygium wilfordii* (TW) or from other known sources. The TW plant is found in the Fujian Province and other southern provinces of China; TW plant material can generally be obtained in China or through commercial sources in the United States. Methods for preparing triptolide, tripdiolide and 16-hydroxytriptolide are known in the art and are described, for example, in Kupchan et al. (1972, 1977); Lipsky et al. (1994); Pu et al. (1990); and Ma et al. (1992).

The 5-hydroxy derivative of triptolide can be prepared by selenium dioxide oxidation of triptolide, as described in co-owned U.S. provisional application Ser. No. 60/532,702. Briefly, in a typical preparation, a solution of triptolide and about 2.2 equivalents of selenium dioxide in dioxane is stirred at about 90° C. under $N_2$ for 72 hrs.

Incubation of triptolide with *Cunninghamella blakesleana*, as described by L. Ning et al. (*Tetrahedron* 59(23):4209-4213, 2003) produces the above hydroxylated derivatives as well as 1β-hydroxytriptolide, triptolidenol (15-hydroxytriptolide), 19α-hydroxytriptolide, and 19β-hydroxytriptolide.

Compounds of formula I can be prepared by reaction of hydroxyl-protected triptolide with a strong base, such as LDA, followed by alkylation of the intermediate enolate. As shown in Scheme 1 below, where methyl iodide was used for alkylation, the isomeric furan alkoxide may also be formed. As described in Example 1, these compounds were isolated and separately deprotected by reaction with mercuric chloride.

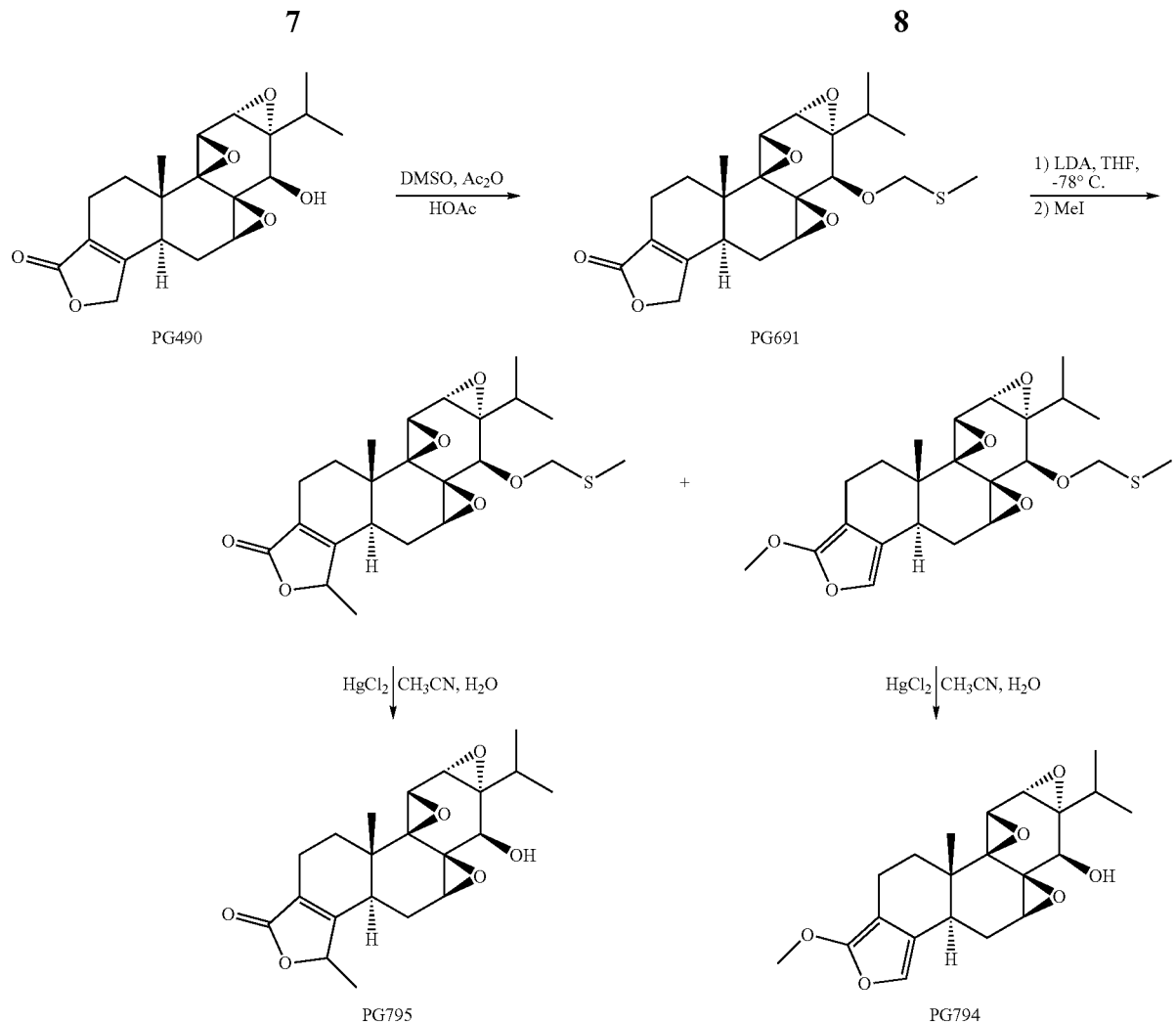
The scheme below illustrates the use of allyl bromide as alkylating agent, to give a compound of formula I in which R¹=allyl (—CH₂CH═CH₂). Similarly, benzyl bromide was employed to give a compound of formula I in which R¹=benzyl (—CH₂C₆H₅).
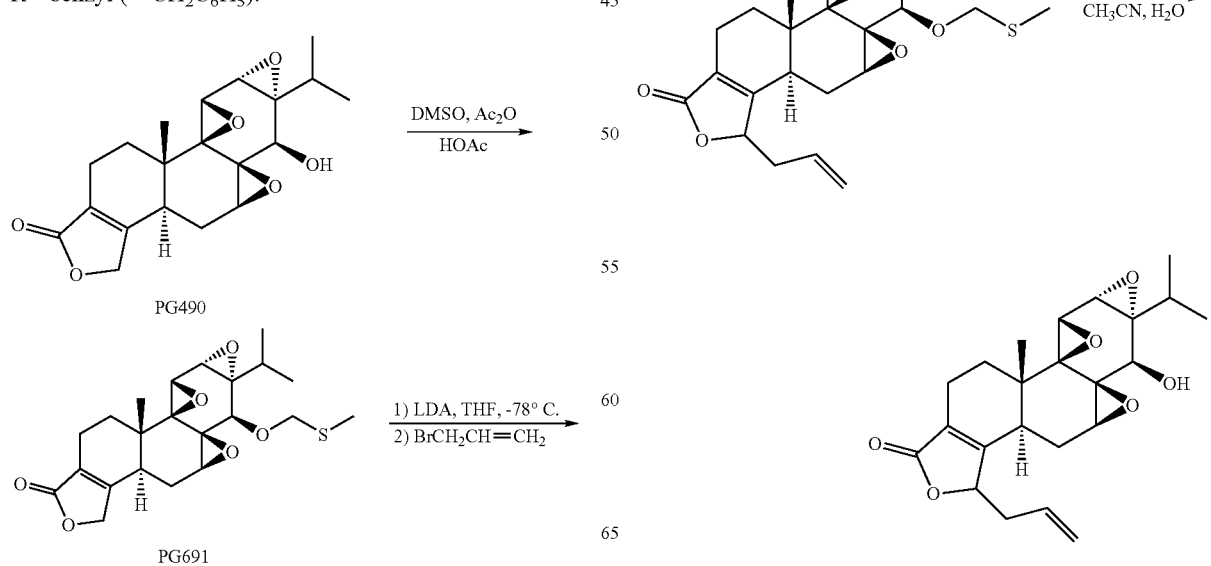

Reaction of the intermediate enolate with a ketone, as shown below, can be used to generate an alcohol substituent; i.e. a compound of formula I in which $R^1$ is $C(OH)R^4R^5$.

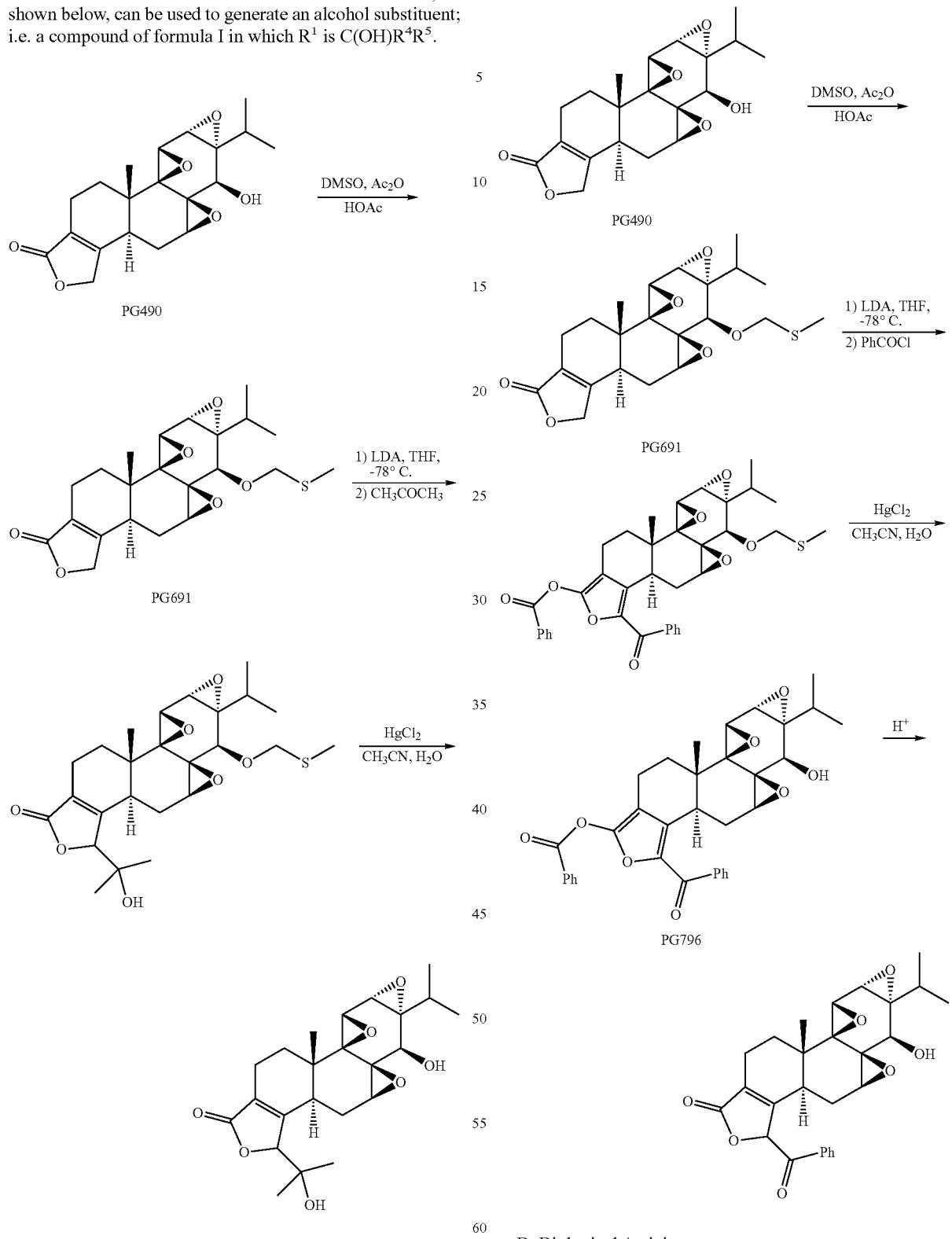

Compounds of formula II can be prepared by reaction of the intermediate enolate with an excess of an acylating reagent, such as an acyl halide, as shown in the Scheme below. The disubstituted compound, in this case, can be hydrolyzed with aqueous acid to generate the monoderivatized conjugated enone.

B. Biological Activity

The cytotoxic activity of a compound of formula I, 19-methyl triptolide (designated PG795) and a compound of formula II, 18-deoxo-19-dehydro-18-benzoyloxy-19-benzoyl triptolide (designated PG796), was evaluated using a standard MTT assay, as described in Example 3. The immunosuppressive activity of these compounds was evaluated in a standard IL-2 inhibition assay, as described in Example 4. The results of these assays are shown in FIGS. 1-4.

Figure 3:
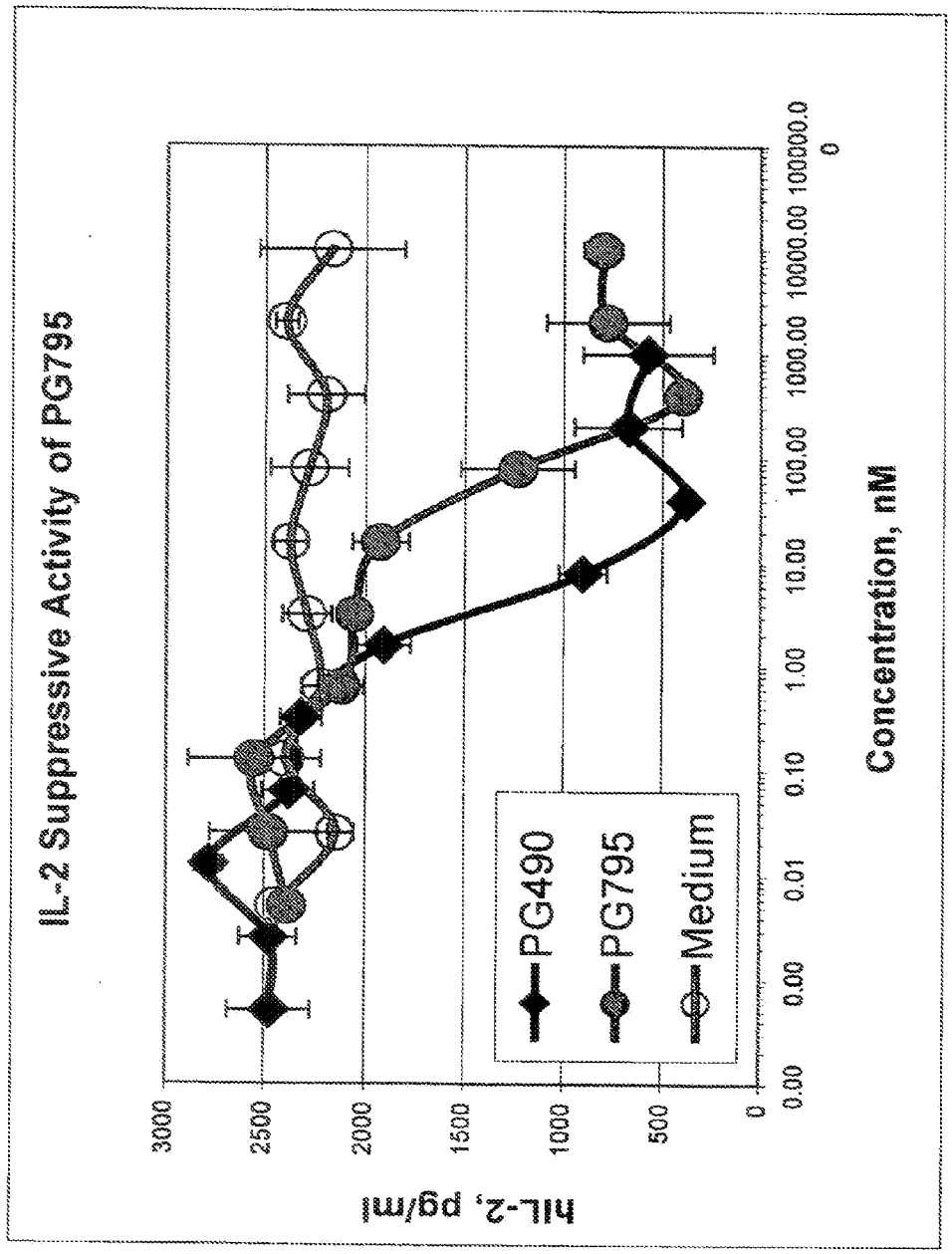
FIG. 3 shows inhibition of IL-2 production in Jurkat cells by a compound of the invention, 19-methyl triptolide (designated PG795), in comparison with triptolide (Example 4)

PG795 showed significant activity in both assays, as shown in FIGS. 1 and 3, though it was less active than triptolide (designated PG490 in the Figures).

Figure 2:
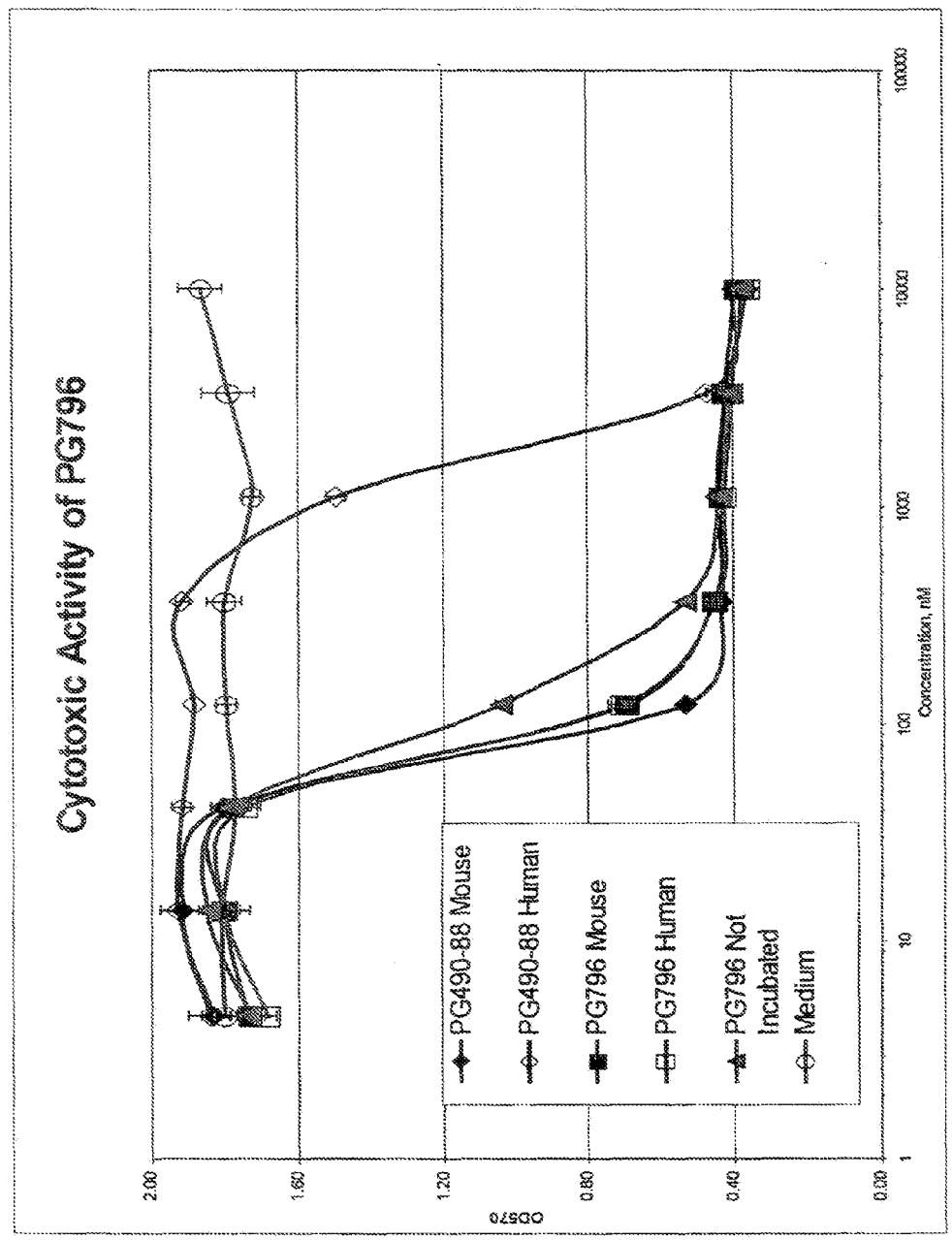
FIG. 2 shows the cytotoxic effect in Jurkat cells of a compound of the invention, 18-deoxo-19-dehydro-18-benzoyloxy-19-benzoyl triptolide (designated PG796), in comparison with triptolide 14-succinate (designated PG490-88), with and without pre-incubation in mouse or human serum (Example 3)
Figure 4:
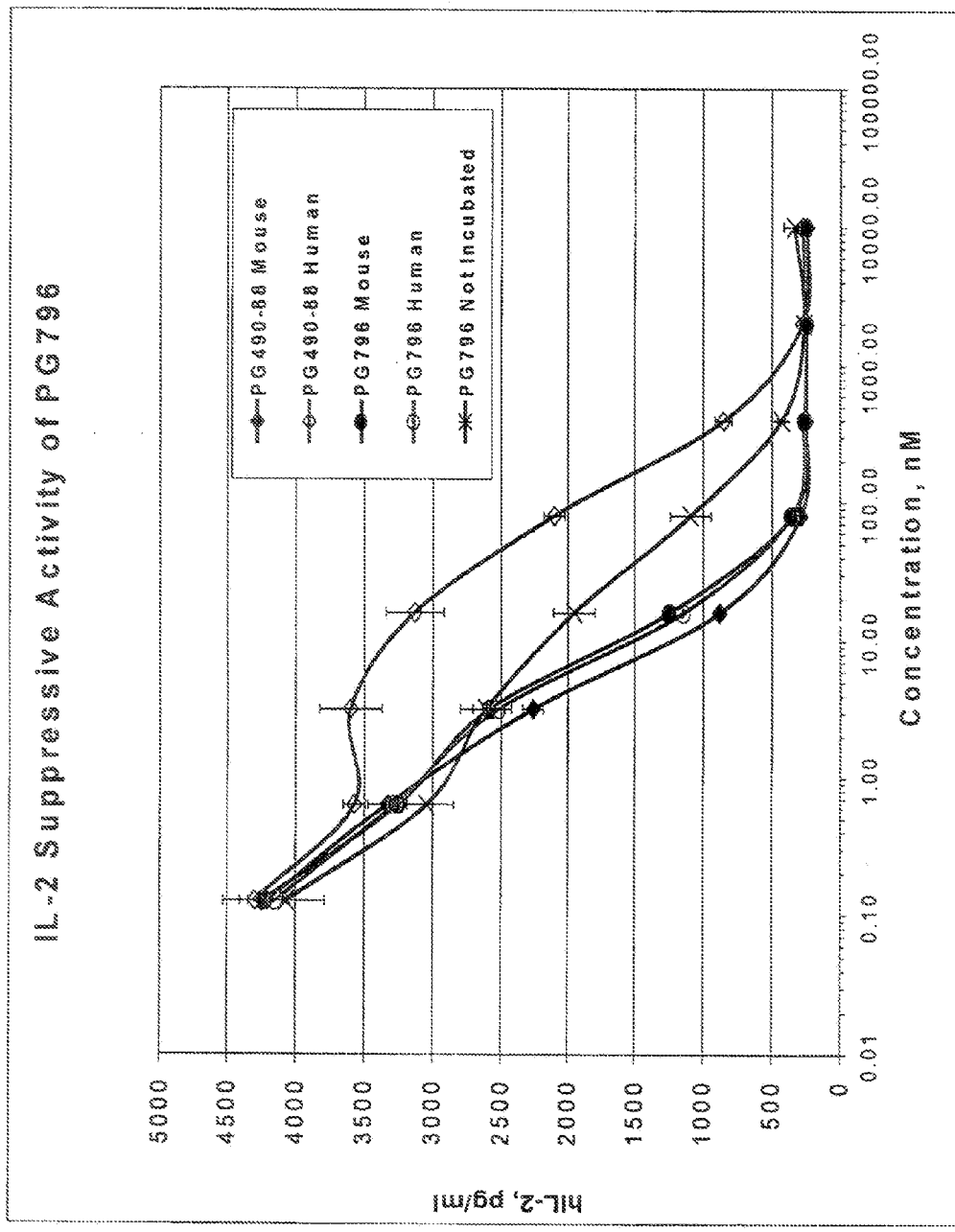
FIG. 4 shows inhibition of IL-2 production in Jurkat cells by PG796, in comparison with triptolide 14-succinate, with and without pre-incubation in mouse or human serum (Example 4).

PG796 showed a higher level of activity in both assays than the known prodrug, triptolide 14-succinate (designated PG490-88), as shown in FIGS. 2 and 4. In particular, triptolide 14-succinate incubated in human serum was much less active in these assays than triptolide 14-succinate incubated in mouse serum, while PG796 showed high, and essentially equivalent, activity in both cases. (Incubation is expected to convert triptolide 14-succinate to triptolide and PG796 to the monoderivatized compound, 19-benzoyl triptolide, shown in the above synthetic scheme.)

In addition, PG476 showed nearly equivalent activity when unincubated, suggesting that the compound is active in its original (i.e. non-hydrolyzed) form.

III. Therapeutic Compositions

Formulations containing the triptolide derivatives of the invention may take the form of solid, semi-solid, lyophilized powder, or liquid dosage forms, such as tablets, capsules, powders, sustained-release formulations, solutions, suspensions, emulsions, ointments, lotions, or aerosols, preferably in unit dosage forms suitable for simple administration of precise dosages. The compositions typically include a conventional pharmaceutical carrier or excipient and may additionally include other medicinal agents, carriers, or adjuvants.

Preferably, the composition includes about 0.5% to 75% by weight of a compound or compounds of the invention, with the remainder consisting of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of nontoxic auxiliary substances such as wetting agents, emulsifying agents, or buffers.

The composition may be administered to a subject orally, transdermally or parenterally, e.g., by intravenous, subcutaneous, intraperitoneal, or intramuscular injection. For use in oral liquid preparation, the composition may be prepared as a solution, suspension, emulsion, or syrup, being supplied either in liquid form or a dried form suitable for hydration in water or normal saline. For parenteral administration, an injectable composition for parenteral administration will typically contain the triptolide derivative in a suitable intravenous solution, such as sterile physiological salt solution.

Liquid compositions can be prepared by dissolving or dispersing the triptolide derivative (about 0.5% to about 20%) and optional pharmaceutical adjuvants in a pharmaceutically acceptable carrier, such as, for example, aqueous saline, aqueous dextrose, glycerol, or ethanol, to form a solution or suspension.

The compound may also be administered by inhalation, in the form of aerosol particles, either solid or liquid, preferably of respirable size. Such particles are sufficiently small to pass through the mouth and larynx upon inhalation and into the bronchi and alveoli of the lungs. In general, particles ranging from about 1 to 10 microns in size, and preferably less than about 5 microns in size, are respirable. Liquid compositions for inhalation comprise the active agent dispersed in an aqueous carrier, such as sterile pyrogen free saline solution or sterile pyrogen free water. If desired, the composition may be mixed with a propellant to assist in spraying the composition and forming an aerosol.

Methods for preparing such dosage forms are known or will be apparent to those skilled in the art; for example, see *Remington's Pharmaceutical Sciences* (20th Ed., Lippincott Williams & Wilkins, 2000). The composition to be administered will contain a quantity of the selected compound in an effective amount for effecting immunosuppression in a subject or apoptosis in a targeted cell.

As described, for example, in Panchagnula et al. (2000), the partition coefficient or logP of a pharmaceutical agent can affect its suitability for various routes of administration, including oral bioavailability. The compounds described herein, by virtue of substitution of fluorine for one or more hydroxyl groups, are expected to have higher calculated logP values than the parent compound, triptolide, making them better candidates for oral availability.

IV. Immunomodulating and Antiinflammatory Treatment

The invention thus includes the use of the invention compounds as immunosuppressive agents, e.g. as an adjunct to transplant procedures or in treatment of autoimmune disease. The compounds of the invention are effective to inhibit immune responses, such as production of cytokines, in cells or organisms. As shown in FIGS. 3-4, a compound of formula I, 19-methyl triptolide (designated PG795), and a compound of formula II, 18-deoxo-19-dehydro-18-benzoyloxy-19-benzoyl triptolide (designated PG796), inhibited IL-2 production in Jurkat cells (see Example 4) in a dose-dependent manner.

Immunoregulatory abnormalities have been shown to exist in a wide variety of autoimmune and chronic inflammatory diseases, including systemic lupus erythematosis, chronic rheumatoid arthritis, type I and II diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, Graves opthalmopathy and asthma. Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow transplant or other transplant of hematopoietic stem cells from a donor tissue source containing mature lymphocytes, the transferred lymphocytes recognize the host tissue antigens as foreign. These cells become activated and mount an attack upon the host (a graft-versus-host response) that can be life-threatening. Moreover, following an organ transplant, the host lymphocytes recognize the foreign tissue antigens of the organ graft and mount cellular and antibody-mediated immune responses (a host-versus-graft response) that lead to graft damage and rejection.

One result of an autoimmune or a rejection reaction is tissue destruction caused by inflammatory cells and the mediators they release. Anti-inflammatory agents such as NSAIDs act principally by blocking the effect or secretion of these mediators but do nothing to modify the immunologic basis of the disease. On the other hand, cytotoxic agents, such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

The compositions of the present invention are useful in applications for which triptolide and its prodrugs and other derivatives have proven effective, e.g. in immunosuppression therapy, as in treating an autoimmune disease, preventing transplantation rejection, or treating or preventing graft-versus-host disease (GVHD). See, for example, co-owned U.S. Pat. No. 6,150,539, which is incorporated herein by reference. Triptolide and the present derivatives are also useful for treatment of other inflammatory conditions, such as traumatic inflammation, and in reducing male fertility.

The compositions are useful for inhibiting rejection of a solid organ transplant, tissue graft, or cellular transplant from an incompatible human donor, thus prolonging survival and function of the transplant, and survival of the recipient. This use would include, but not be limited to, solid organ transplants (such as heart, kidney and liver), tissue grafts (such as skin, intestine, pancreas, gonad, bone, and cartilage), and cellular transplants (such as cells from pancreas, brain and nervous tissue, muscle, skin, bone, cartilage and liver).

The compositions are also useful for inhibiting xenograft (interspecies) rejection; i.e. in preventing the rejection of a solid organ transplant, tissue graft, or cellular transplant from a non-human animal, whether natural in constitution or bioengineered (genetically manipulated) to express human genes, RNA, proteins, peptides or other non-native, xenogeneic molecules, or bioengineered to lack expression of the animal's natural genes, RNA, proteins, peptides or other normally expressed molecules. The invention also includes the use of a composition as described above to prolong the survival of such a solid organ transplant, tissue graft, or cellular transplant from a non-human animal.

Also included are methods of treatment of autoimmune diseases or diseases having autoimmune manifestations, such as Addison's disease, autoimmune hemolytic anemia, autoimmune thyroiditis, Crohn's disease, diabetes (Type I), Graves' disease, Guillain-Barre syndrome, systemic lupus erythematosis (SLE), lupus nephritis, multiple sclerosis, myasthenia gravis, psoriasis, primary biliary cirrhosis, rheumatoid arthritis and uveitis, asthma, atherosclerosis, Hashimoto's thyroiditis, allergic encephalomyelitis, glomerulonephritis, and various allergies.

Further uses may include the treatment and prophylaxis of inflammatory and hyperproliferative skin diseases and cutaneous manifestations of immunologically mediated illnesses, such as psoriasis, atopic dermatitis, pemphigus, urticaria, cutaneous eosinophilias, acne, and alopecia areata; various eye diseases such as conjunctivitis, uveitis, keratitis, and sarcoidosis; inflammation of mucous and blood vessels such as gastric ulcers, vascular damage caused by ischemic diseases and thrombosis, ischemic bowel diseases, inflammatory bowel diseases, and necrotizing enterocolitis; intestinal inflammations/allergies such as Coeliac diseases and ulcerative colitis; renal diseases such as interstitial nephritis, Good-pasture's syndrome, hemolytic-uremic syndrome and diabetic nephropathy; hematopoietic diseases such as idiopathic thrombocytopenia purpura and autoimmune hemolytic anemia; skin diseases such as dermatomyositis and cutaneous T cell lymphoma; circulatory diseases such as arteriosclerosis and atherosclerosis; renal diseases such as ischemic acute renal insufficiency and chronic renal insufficiency; and Behcet's disease.

The compositions and method of the invention are also useful for the treatment of inflammatory conditions such as asthma, both intrinsic and extrinsic manifestations, for example, bronchial asthma, allergic asthma, intrinsic asthma, extrinsic asthma and dust asthma, particularly chronic or inveterate asthma (for example, late asthma and airway hyperresponsiveness). The composition and method may also be used for treatment of other inflammatory conditions, including traumatic inflammation, inflammation in Lyme disease, chronic bronchitis (chronic infective lung disease), chronic sinusitis, sepsis associated acute respiratory distress syndrome, and pulmonary sarcoidosis. For treatment of respiratory conditions such as asthma, the composition is preferably administered via inhalation, but any conventional route of administration may be useful.

In treating an autoimmune condition, the patient is given the composition on a periodic basis, e.g., 1-2 times per week, at a dosage level sufficient to reduce symptoms and improve patient comfort. For treating rheumatoid arthritis, in particular, the composition may be administered by intravenous injection or by direct injection into the affected joint. The patient may be treated at repeated intervals of at least 24 hours, over a several week period following the onset of symptoms of the disease in the patient. The dose that is administered is preferably in the range of 1-25 mg/kg patient body weight per day, with lower amounts being preferred for parenteral administration, and higher amounts being preferred for oral administration. Optimum dosages can be determined by routine experimentation according to methods known in the art.

For therapy in transplantation rejection, the method is intended particularly for the treatment of rejection of heart, kidney, liver, cellular, and bone marrow transplants, and may also be used in the treatment of GVHD. The treatment is typically initiated perioperatively, either soon before or soon after the surgical transplantation procedure, and is continued on a daily dosing regimen, for a period of at least several weeks, for treatment of acute transplantation rejection. During the treatment period, the patient may be tested periodically for immunosuppression level, e.g., by a mixed lymphocyte reaction involving allogeneic lymphocytes, or by taking a biopsy of the transplanted tissue.

In addition, the composition may be administered chronically to prevent graft rejection, or in treating acute episodes of late graft rejection. As above, the dose administered is preferably 1-25 mg/kg patient body weight per day, with lower amounts being preferred for parenteral administration, and higher amounts for oral administration. The dose may be increased or decreased appropriately, depending on the response of the patient, and over the period of treatment, the ability of the patient to resist infection.

In treatment or prevention of graft-versus-host disease, resulting from transplantation into a recipient of matched or mismatched bone marrow, spleen cells, fetal tissue, cord blood, or mobilized or otherwise harvested stem cells, the dose is preferably in the range 0.25-2 mg/kg body weight/day, preferably 0.5-1 mg/kg/day, given orally or parenterally.

Also within the scope of the invention is a combination therapy comprising a compound of formula I and one or more conventional immunosuppressive agents. These immunosuppressant agents within the scope of this invention include, but are not limited to, Imurek® (azathioprine sodium), brequinar sodium, Spanidin™ (gusperimus trihydrochloride, also known as deoxyspergualin), mizoribine (also known as bredinin), Cellcept® (mycophenolate mofetil), Neoral® (Cyclosporin A; also marketed as a different formulation under the trademark Sandimmune®), Prograf™ (tacrolimus, also known as FK-506), Rapimmune® (sirolimus, also known as rapamycin), leflunomide (also known as HWA-486), Zenapax®, glucocortcoids, such as prednisolone and its derivatives, antibodies such as orthoclone (OKT3), and antithymyocyte globulins, such as thymoglobulins. The compounds are useful as potentiators when administered concurrently with another immunosuppressive drug for immunosuppressive treatments as discussed above. A conventional immunosuppressant drug, such as those above, may thus be administered in an amount substantially less (e.g. 20% to 50% of the standard dose) than when the compound is administered alone. Alternatively, the invention compound and immunosuppressive drug are administered in amounts such that the resultant immunosuppression is greater than what would be expected or obtained from the sum of the effects obtained with the drug and invention compound used alone. Typically, the immunosuppressive drug and potentiator are administered at regular intervals over a time period of at least 2 weeks.

The compositions of the invention may also be administered in combination with a conventional anti-inflammatory drug (or drugs), where the drug or amount of drug administered is, by itself, ineffective to induce the appropriate suppression or inhibition of inflammation.

Immunosuppressive activity of compounds in vivo can be evaluated by the use of established animal models known in the art. Such assays may be used to evaluate the relative effectiveness of immunosuppressive compounds and to estimate appropriate dosages for immunosuppressive treatment. These assays include, for example, a well-characterized rat model system for allografts, described by Ono and Lindsey (1969), in which a transplanted heart is attached to the abdominal great vessels of an allogeneic recipient animal, and the viability of the transplanted heart is gauged by the heart's ability to beat in the recipient animal. A xenograft model, in which the recipient animals are of a different species, is described by Wang (1991) and Murase (1993). A model for evaluating effectiveness against GVHD involves injection of normal F1 mice with parental spleen cells; the mice develop a GVHD syndrome characterized by splenomegaly and immunosuppression (Korngold, 1978; Gleichmann, 1984). Single cell suspensions are prepared from individual spleens, and microwell cultures are established in the presence and absence of concanavalin A to assess the extent of mitogenic responsiveness.

V. Anticancer Treatment

As shown in FIGS. 1-2, a compound of formula I, 19-methyl triptolide (designated PG795), and a compound of formula II, 18-deoxo-19-dehydro-18-benzoyloxy-19-benzoyl triptolide (designated PG796), were each cytotoxic to Jurkat cells (see Example 2) in a dose-dependent manner. The invention thus includes the use of the invention compounds as cytotoxic agents, particularly to treat cancers. As used herein, "cancer" refers to all types of cancer or neoplasm or malignant tumors found in mammals especially humans, including leukemias, sarcomas, carcinomas and melanoma.

The term "leukemia" refers broadly to progressive, malignant diseases of the blood-forming organs and is generally characterized by a distorted proliferation and development of leukocytes and their precursors in the blood and bone marrow. The term "sarcoma" generally refers to a tumor which is made up of a substance like the embryonic connective tissue and is generally composed of closely packed cells embedded in a fibrillar or homogeneous substance. The term "melanoma" is taken to mean a tumor arising from the melanocytic system of the skin and other organs. The term "carcinoma" refers to a malignant new growth made up of epithelial cells tending to infiltrate the surrounding tissues and give rise to metastases.

Included, for example, are cancers involving cells derived from reproductive tissue (such as Sertoli cells, germ cells, developing or more mature spermatogonia, spermatids or spermatocytes and nurse cells, germ cells and other cells of the ovary), the lymphoid or immune systems (such as Hodgkin's disease and non-Hodgkin's lymphomas), the hematopoietic system, and epithelium (such as skin, including malignant melanoma, and gastrointestinal tract), solid organs, the nervous system, e.g. glioma (see Y. X. Zhou et al., 2002), and musculo-skeletal tissue. The compounds may be used for treatment of various cancer cell types, including, but not limited to, brain, including medulloblastoma, head and neck, breast, colon, small cell lung, large cell lung, thyroid, testicle, bladder, prostate, liver, kidney, pancreatic, esophogeal, stomach, ovarian, cervical or lymphoma tumors. Treatment of breast, colon, lung, and prostate tumors is particularly contemplated.

The compositions may be administered to a patient afflicted with cancer and/or leukemia by any conventional route of administration, as discussed above. The method is useful to slow the growth of tumors, prevent tumor growth, induce partial regression of tumors, and induce complete regression of tumors, to the point of complete disappearance. The method is also useful in preventing the outgrowth of metastases derived from solid tumors.

The compositions of the invention may be administered as sole therapy or with other supportive or therapeutic treatments not designed to have anti-cancer effects in the subject. The method also includes administering the invention compositions in combination with one or more conventional anti-cancer drugs or biologic protein agents, where the amount of drug(s) or agent(s) is, by itself, ineffective to induce the appropriate suppression of cancer growth, in an amount effective to have the desired anti-cancer effects in the subject. Such anti-cancer drugs include actinomycin D, camptothecin, carboplatin, cisplatin, cyclophosphamide, cytosine arabinoside, daunorubicin, doxorubicin, etoposide, fludarabine, 5-fluorouracil, hydroxyurea, gemcitabine, irinotecan, methotrexate, mitomycin C, mitoxantrone, paclitaxel, taxotere, teniposide, topotecan, vinblastine, vincristine, vindesine, and vinorelbine. Anti-cancer biologic protein agents include tumor necrosis factor (TNF), TNF-related apoptosis inducing ligand (TRAIL), other TNF-related or TRAIL-related ligands and factors, interferon, interleukin-2, other interleukins, other cytokines, chemokines, and factors, antibodies to tumor-related molecules or receptors (such as anti-HER2 antibody), and agents that react with or bind to these agents (such as members of the TNF super family of receptors, other receptors, receptor antagonists, and antibodies with specificity for these agents).

Antitumor activity in vivo of a particular composition can be evaluated by the use of established animal models, as described, for example, in Fidler et al., U.S. Pat. No. 6,620,843. Clinical doses and regimens are determined in accordance with methods known to clinicians, based on factors such as severity of disease and overall condition of the patient.

VI. Other Indications

The compounds of the present invention may also be used in the treatment of certain CNS diseases. Glutamate fulfills numerous physiological functions, including an important role in the pathophysiology of various neurological and psychiatric diseases. Glutamate excitotoxicity and neurotoxicity have been implicated in hypoxia, ischemia and trauma, as well as in chronic neurodegenerative or neurometabolic diseases, Alzheimer's dementia, Huntington's disease and Parkinson's disease. In view of the reported neuroprotective effects of triptolide, particularly protection from glutamate-induced cell death (Q. He et al., 2003; X. Wang et al., 2003), compounds of the invention are envisioned to antagonize the neurotoxic action of glutamates and thus may be a novel therapy for such diseases.

Recent evidence from MS patients in relapse suggests an altered glutamate homeostasis in the brain. Neurotoxic events occurring in MS patients can be responsible for oligodendrocyte and neuronal cell death. Antagonizing glutamate receptor-mediated excitotoxicity by treatment with compounds of this invention may have therapeutic implications in MS patients. Other CNS diseases such as Guillain-Barre syndrome, Meniere's disease, polyneuritis, multiple neuritis, mononeuritis and radiculopathy may also be treated with the compounds of the present invention.

The compounds of the present invention may also be used in the treatment of certain lung diseases. Idiopathic pulmonary fibrosis (PF) is a progressive interstitial lung disease with no known etiology. PF is characterized by excessive deposition of intracellular matrix and collagen in the lung interstitium and gradual replacement of the alveoli by scar tissue as a result of inflammation and fibrosis. As the disease progresses, the increase in scar tissue interferes with the ability to transfer oxygen from the lungs to the bloodstream. A 14-succinimide ester of triptolide has been reported to block bleomycin-induced PF (G. Krishna et al., 2001). Accordingly, the compounds of the present invention may be useful for treatment of PF. Treatment of other respiratory diseases, such as sarcoidosis, fibroid lung, and idiopathic interstitial pneumonia is also considered.

Other diseases involving the lung and envisioned to be treatable by compounds of this invention include Severe Acute Respiratory Syndrome (SARS) and acute respiratory distress syndrome (ARDS). In particular, with respect to SARS, the reduction of virus content (SARS-CoV) before the peak of the disease process and the usefulness of corticosteroid treatment, as noted below, suggest that the development of the most severe, life-threatening effects of SARS may result from the exaggerated response of the body to the infection (immune hyperactivity) rather than effects of the virus itself (See also copending and co-owned U.S. provisional application Ser. No. 60/483,335, which is incorporated herein by reference.) Corticosteroid treatment has been used in SARS patients to suppress the massive release of cytokines that may characterize the immune hyperactive phase, in the hope that it will stop the progression of pulmonary disease in the next phase. Corticosteroid treatment has produced good clinical results in reduction of some of the major symptoms of SARS. However, there are several treatment-related side effects, and there is a clear need for more selective immunosuppressive and/or antiinflammatory agents.

EXAMPLES

The following examples are intended to illustrate but not in any way limit the invention.

Example 1

Preparation of 19-Methyl Triptolide (PG795)

A. Protection of 14-Hydroxyl Group

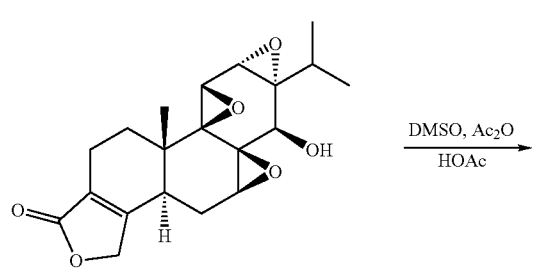

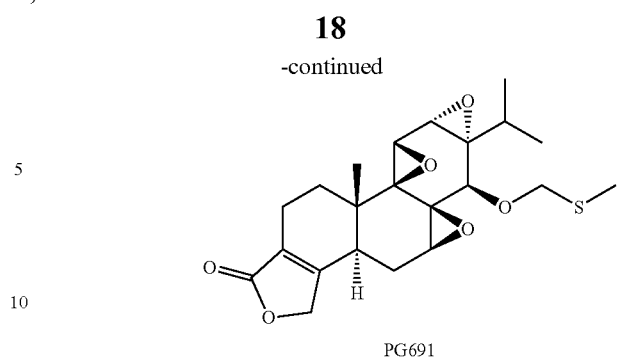

PG691

To a solution of triptolide (designated PG490) (0.56 g, 1.6 mmol) in DMSO (8.5 mL, 0.12 mol) was added acetic acid (28 mL, 0.49 mol) and acetic anhydride (5.6 mL, 59 mol). The clear colorless solution was stirred at room temperature for five days. The reaction mixture was poured into 200 mL of water and neutralized with solid sodium bicarbonate, added in portions. The mixture was extracted with ethyl acetate (3×150 mL), and the extract was dried over anhydrous sodium sulfate. Concentration under reduced pressure gave the crude product as an oil. Silica gel column chromatography purification (3:2 hexanes/ethyl acetate) gave the 14-(methylthio)methoxy derivative (designated PG691) (0.45 g, 69%) as a white foam. $^1$H NMR (CDCl$_3$) δ 0.83 (d, J=6.8 Hz, 3H), 1.01 (d, J=6.8 Hz, 3H), 1.10 (s, 3H), 1.20 (m, 1H), 1.61 (m, 1H), 1.92 (dd, J=14.7, 13.4 Hz, 1H), 2.19 (s, 3H), 2.10-2.42 (m, 4H), 2.70 (m, 1H), 3.24 (d, J=5.5 Hz, 1H), 3.51 (d, J=3.1 Hz, 1H), 3.68 (s, 1H), 3.79 (d, J=3.1 Hz, 1H), 4.68 (m, 2H), 4.95 (d, J=11.8 Hz, 1H), 5.09 (d, J=11.8 Hz, 1H)

B. Methylation

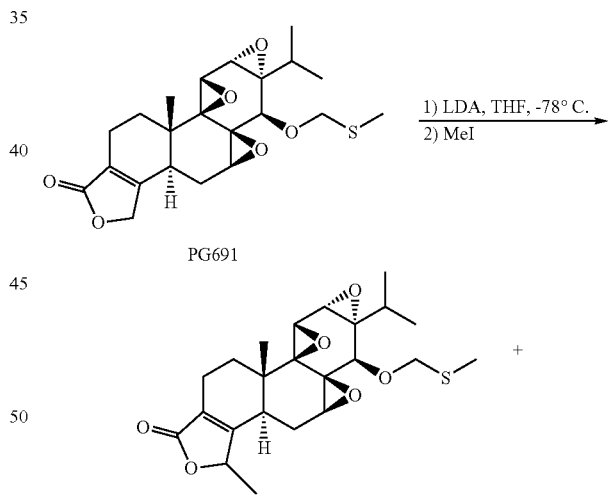

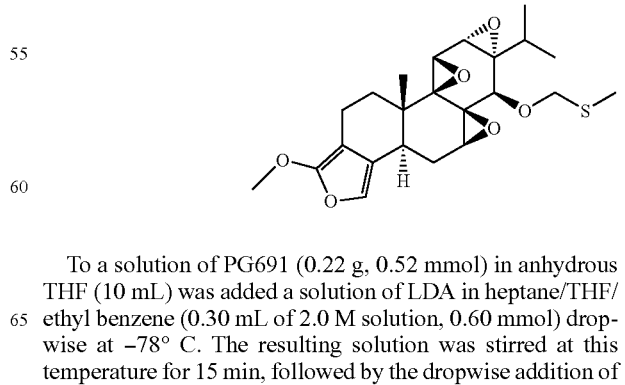

To a solution of PG691 (0.22 g, 0.52 mmol) in anhydrous THF (10 mL) was added a solution of LDA in heptane/THF/ethyl benzene (0.30 mL of 2.0 M solution, 0.60 mmol) dropwise at −78° C. The resulting solution was stirred at this temperature for 15 min, followed by the dropwise addition of methyl iodide (50 μL, 0.80 mmol). The reaction mixture was stirred at −78° C. for 2 h, then allowed to come to room temperature overnight.

The reaction mixture was neutralized with 1N HCl, and the biphasic solution was extracted with EtOAc (10 mL×3). The EtOAc solution was washed with 5% aqueous sodium thiosulfate (10 mL×2) and dried over anhydrous sodium sulfate. Concentration under reduce pressure gave an oil. Column purification (silica gel, 3:2 hexanes/ethyl acetate) gave two products, methylthiomethyl protected 19-methyltriptolide (45.9 mg, 20%), $^1$H NMR (CDCl$_3$) δ 0.84 (d, J=6.9 Hz, 3H), 1.03 (d, J=6.9 Hz, 3H), 1.10 (s, 3H), 1.16 (m, 1H), 1.44 (d, J=6.6 Hz, 3H), 1.59 (m, 1H), 1.92 (t, J=14.0 Hz, 1H), 2.19 (s, 3H), 2.10-2.42 (m, 4H), 2.62 (m, 1H), 3.25 (d, J=5.5 Hz, 1H), 3.31 (d, J=3.1 Hz, 1H), 3.69 (s, 1H), 3.79 (d, J=3.2 Hz, 1H), 4.89 (m, 1H), 4.95 (d, J=11.8 Hz, 1H), 5.09 (d, J=11.8 Hz, 1H), and methylthiomethyl protected 18-methoxyfuranotriptolide (33.1 mg, 15%), $^1$H NMR (CDCl$_3$) δ 0.84 (d, J=6.9 Hz, 3H), 1.01 (s, 3H), 1.02 (d, J=6.9 Hz, 3H), 1.30 (s, 3H), 1.37 (m, 2H), 1.69 (m, 2H), 1.95 (dd, J=15.0, 12.6 Hz, 1H), 2.10 (m, 1H), 2.19 (s, 3H), 2.27-2.47 (m, 2H), 3.19 (d, J=5.3 Hz, 1H), 3.54 (d, J=3.3 Hz, 1H), 3.67 (s, 1H), 3.93 (d, J=3.3 Hz, 1H), 4.94 (d, J=11.9 Hz, 1H), 5.08 (d, J=11.9 Hz, 1H), 6.44 (d, J=2.0 Hz, 1H).

C. Deprotection

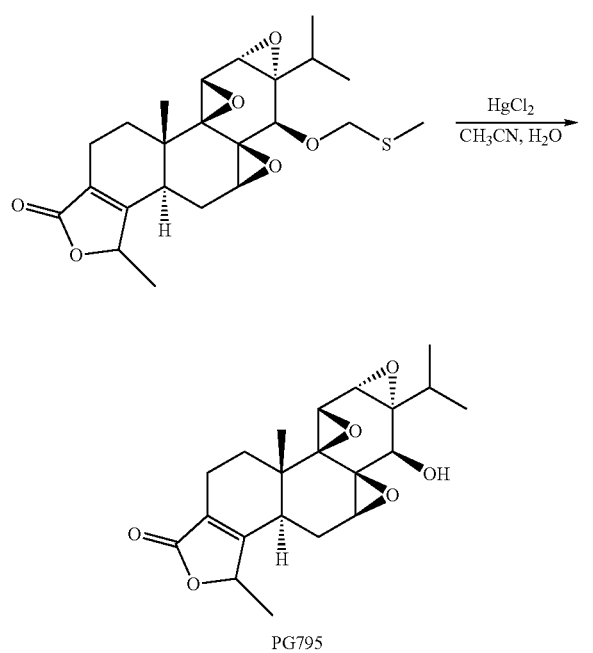

To a solution of methylthiomethyl protected 19-methyltriptolide, prepared as described above (45.9 mg, 0.106 mmol), in 1.5 mL acetonitrile/water (4:1) was added mercuric chloride (0.285 g, 1.05 mmol) in one portion. The resulting solution was stirred at room temperature overnight. The white solid which precipitated from the solution was removed by filtration through Celite® and rinsed with ethyl acetate. The EtOAc solution was washed twice with 5% aqueous NH$_4$OAc. The organic phase was dried (Na$_2$SO$_4$) and concentrated under reduced pressure to give the crude product. Purification by column chromatography (silica gel, 1:1 hexanes/ethyl acetate) gave the pure product (39.5 mg, 99%). $^1$H NMR (CDCl$_3$) δ 0.88 (d, J=6.8 Hz, 3H), 1.01 (d, J=6.8 Hz, 3H), 1.11 (s, 3H), 1.16 (dt, J=11.5, 2.0 Hz, 1H), 1.43 (d, J=6.6 Hz, 3H), 1.54 (ddd, J=12.4, 6.4, 1.3 Hz, 1H), 1.92 (dd, J=14.9, 13.4 Hz, 1H), 2.10-2.36 (m, 4H), 2.62 (m, 1H), 2.74 (d, J=10.8 Hz, 1H), 3.38 (d, J=5.5 Hz, 1H), 3.42 (d, J=10.8 Hz, 1H), 3.53 (dd, J=3.1, 0.9 Hz, 1H), 3.90 (d, J=3.1 Hz, 1H), 4.88 (m, 1H); IR (CH$_2$Cl$_2$) 1754, 1047 cm$^{-1}$.

Example 2

Preparation of 18-deoxo-19-dehydro-18-benzoyloxy-19-benzoyl triptolide (PG796)

A. Acylation

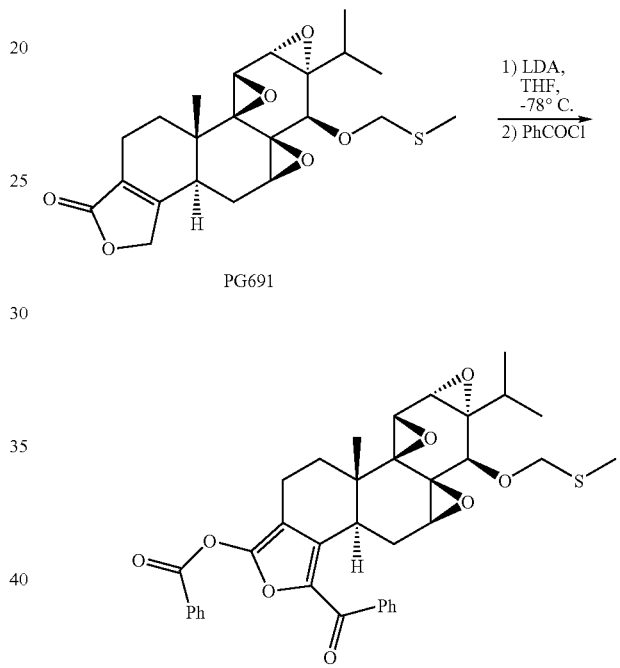

To a solution of PG691, prepared as described above (73.1 mg, 0.174 mmol), in anhydrous THF (5 mL) was added a solution of LDA in heptane/THF/ethyl benzene (0.17 mL of 2.0 M solution, 0.34 mmol) dropwise at −78° C. The resulting solution was stirred at this temperature for 15 min, followed by the dropwise addition of neat benzoyl chloride (100 μL, 0.86 mmol). The reaction was stirred at −78° C. for 2 h. The reaction was quenched with water and the mixture was extracted with ethyl acetate (25 mL×3). The combined organic solution was dried over anhydrous over anhydrous sodium sulfate. Concentration under reduce pressure gave an oil. Column purification (silica gel, 3:2 hexanes/ethyl acetate) gave the 14-protected product (51.2 mg, 47%). $^1$H NMR (CDCl$_3$) δ 0.78 (d, J=6.8 Hz, 3H), 0.91 (d, J=6.8 Hz, 3H), 1.13 (s, 3H), 1.17 (m, 1H), 1.58 (m, 1H), 1.86 (m, 1H), 2.13 (s, 3H), 2.17-2.39 (m, 3H), 2.45 (d, J=6.0 Hz, 1H), 2.58-2.76 (m, 2H), 3.21 (s, 1H), 3.39 (d, J=3.1 Hz, 1H), 3.70 (d, J=3.1 Hz, 1H), 4.85 (d, J=11.87 Hz, 1H), 4.95 (d, J=11.8 Hz, 1H), 7.34-7.48 (m, 3H), 7.56-7.65 (m, 2H), 7.65-7.71 (m, 1H), 7.71-7.78 (m, 2H), 8.21-8.29 (m, 2H).

B. Deprotection

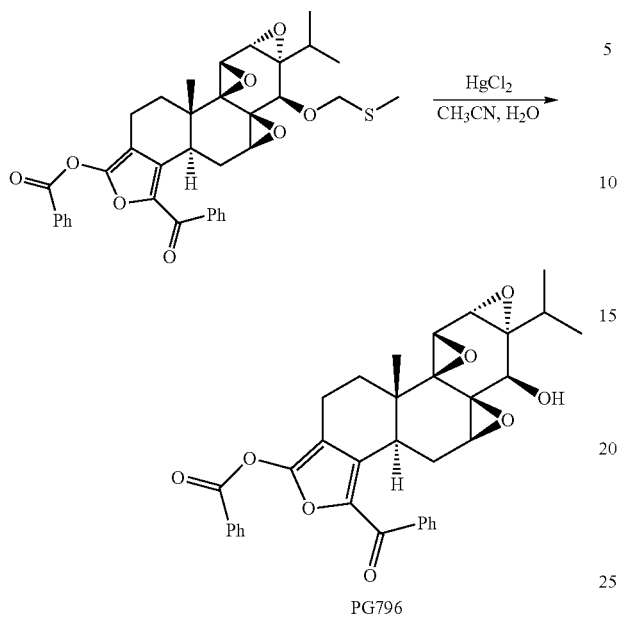

PG796

To a solution of the 14-methylthiomethyl protected product, prepared as described above (51.2 mg, 0.0814 mmol), in 1.5 mL acetonitrile/water (4:1) was added mercuric chloride (0.22 g, 0.81 mmol) in one portion. The resulting solution was stirred at room temperature overnight. The white solid which precipitated from the solution was removed by filtration through Celite® and rinsed with ethyl acetate. The EtOAc solution was washed twice with 5% aqueous $NH_4OAc$. The organic phase was dried ($Na_2SO_4$) and concentrated under reduced pressure to give the crude product. Purification by column chromatography provided the pure product (32.8 mg, 71%). $^1$H NMR (CDCl$_3$) δ 0.82 (d, J=6.9 Hz, 3H), 0.92 (d, J=6.9 Hz, 3H), 1.15 (s, 3H), 1.17 (m, 1H), 1.54 (m, 1H), 1.88 (m, 1H), 2.18 (septet, J=6.9 Hz), 2.30-2.40 (m, 2H), 2.53 (d, J=10.4 Hz, 1H), 2.56 (d, J=7.1 Hz, 1H), 2.61 (m, 1H), 2.72 (ddd, J=15.0, 6.4, 4.2 Hz, 2H), 2.98 (d, J=10.2 Hz, 1H), 3.40 (d, J=3.0 Hz, 1H), 3.81 (d, J=3.0 Hz, 1H), 7.35-7.47 (m, 3H), 7.54-7.63 (m, 2H), 7.63-7.71 (m, 1H), 7.71-7.78 (m, 2H), 8.21-8.28 (m, 2H); IR (CH$_2$Cl$_2$) 1768, 1751, 1236, 1123 cm$^{-1}$.

Example 3

Cytotoxicity (MTT) Assay

Test compounds were dissolved in DMSO at a concentration of 20 mM. Further dilutions were done in RPMI1640 medium (GIBCO, Rockville, Md.) supplemented with 10% Fetal Calf Serum (HyClone Laboratories, Logan, Utah).

Cytotoxicity of the compounds was determined in a standard MTT assay using Cell Proliferation Kit I (#1 465 007, Roche Diagnostics, Mannheim, Germany). Briefly, human T cell lymphoma (Jurkat) cells (4×10$^5$ per well) were cultured for 24 h, in 96-well tissue culture plates, in the presence of serial three-fold dilutions of test compounds or medium containing the same concentration of DMSO as in the test samples at each dilution point. The cultures were then supplemented with 10 μl/well MTT reagent for 4 h and then with 0.1 ml/well solubilizing reagent for an additional 16 h. Optical density at 570 nm (OD$_{570}$) was measured on a ThermoScan microplate reader (Molecular Devices, Menlo Park, Calif.).

The data is presented as OD$_{570}$ values versus concentration of the compounds. The results for 19-methyl triptolide (PG795), compared with triptolide (PG490) and a medium control, are given in FIG. 1. The results for PG796, compared with triptolide 14-succinate (PG490-88) and a medium control, are given in FIG. 2. In this case, data is provided for both compounds incubated in human serum and in mouse serum, and for PG796 without incubation.

Example 4

IL-2 Production Assay

Test samples were diluted to 1 mM in complete tissue culture medium. Aliquots were placed in microculture plates that had been coated with anti-CD3 antibody (used to stimulate the production of IL-2 by Jurkat cells), and serial dilutions were prepared so that the final concentration would encompass the range of 0.001 to 10,000 nM in log increments. Cells from an exponentially expanding culture of Jurkat human T cell line (#TIB-152 obtained from American Type Culture Collection, Manassas, Va.) were harvested, washed once by centrifugation, re-suspended in complete tissue culture medium, and diluted to a concentration of 2×10$^6$ cells/ml. A volume of 50 μl of Jurkat cells (1×10$^5$ cells) was added to wells containing 100 μl of the diluted compounds, 50 μl of PMA (10 ng/ml) was added to each well, and the plates were incubated at 37° C. in a 5% CO$_2$ incubator. After 24 hours, the plates were centrifuged to pellet the cells, 150 μl of supernatant was removed from each well, and the samples were stored at −20° C. The stored supernatants were analyzed for human IL-2 concentration using the Luminex 100 (Luminex Corporation, Austin, Tex.), Luminex microspheres coupled with anti-IL-2 capture antibody, and fluorochrome-coupled anti-IL-2 detection antibody. The data were expressed as pg/ml of IL-2.

The data were plotted as the concentration of compound versus IL-2 concentration. The results for 19-methyl triptolide (PG795), compared with triptolide (PG490) and a medium control, are given in FIG. 3. The results for PG796, compared with triptolide 14-succinate (PG490-88) and a medium control, are given in FIG. 4. In this case, data is provided for both compounds incubated in human serum and in mouse serum, and for PG796 without incubation.

It is claimed:

1. A compound having the structure I:

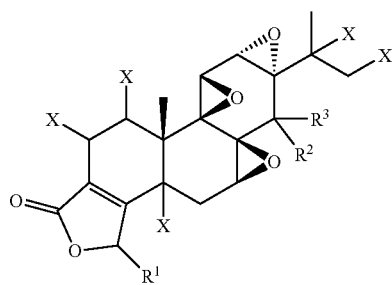

where
- $R^1$ is alkyl, alkenyl, alkynyl, arylalkyl, aryl, arylacyl, or $C(OH)R^4R^5$,
  - wherein $R^4$ and $R^5$ are independently hydrogen, alkyl, cycloalkyl, alkenyl, or cycloalkenyl, any of which, excepting hydrogen, may be substituted with alkoxy, hydroxy, acyloxy, or aryl;
- $CR^2R^3$ is CHOH or C=O; and
- at most one of the groups X is hydroxyl, and the remaining groups X are hydrogen.

2. The compound of claim 1, wherein $CR^2R^3$ is CHOH.

3. The compound of claim 2, wherein $CR^2R^3$ is CHOH (β-hydroxy).

4. The compound of claim 1, wherein each X is hydrogen.

5. The compound of claim 1, wherein each said alkyl, alkenyl, alkynyl, alkoxy, and acyloxy includes at most four carbon atoms, each said cycloalkyl and cycloalkenyl includes at most six carbon atoms, and each said aryl is monocyclic and non-heterocyclic.

6. The compound of claim 5, wherein $R^1$ is alkyl, alkenyl or $C(OH)R^4R^5$.

7. The compound of claim 6, wherein $R^4$ and $R^5$ are independently hydrogen, alkyl or alkenyl.

8. The compound of claim 1, wherein $R^1$ is alkyl or hydroxyalkyl.

9. The compound of claim 8, wherein $R^1$ is $C_1$-$C_3$ alkyl or hydroxyalkyl.

10. The compound of claim 9, wherein $R^1$ is methyl.

11. The compound of claim 1, wherein $R^1$ is arylacyl.

12. The compound of claim 11, wherein $R^1$ is benzoyl $(C(O)C_6H_5)$.

13. The compound of claim 4, wherein $R^1$ is benzoyl.

* * * * *